US006117974A

United States Patent [19]
Gilon et al.

[11] Patent Number: 6,117,974
[45] Date of Patent: *Sep. 12, 2000

[54] LIBRARIES OF BACKBONE-CYCLIZED PEPTIDOMIMETICS

[75] Inventors: Chaim Gilon, Jerusalem; Vered Hornik, Rehovot, both of Israel

[73] Assignees: Peptor Limited, Rehovot; Yissum Research Development Company of The Hebrew University in Jerusalem, Jerusalem, both of Israel

[*] Notice: This patent is subject to a terminal disclaimer.

[21] Appl. No.: 08/569,042

[22] Filed: Dec. 7, 1995

Related U.S. Application Data

[63] Continuation-in-part of application No. 08/444,135, May 18, 1995, Pat. No. 5,723,575, which is a continuation-in-part of application No. 07/955,380, Oct. 1, 1992, abandoned.

[30] Foreign Application Priority Data

Oct. 2, 1991 [IL] Israel .......................................... 99628
Aug. 29, 1995 [IL] Israel ........................................ 115096

[51] Int. Cl.[7] .......................... A61K 38/12; A61K 38/00; C07K 1/046

[52] U.S. Cl. ........................... 530/317; 530/333; 436/501

[58] Field of Search .................................. 436/512, 501, 436/518; 530/333, 334, 317

[56] References Cited

U.S. PATENT DOCUMENTS

| | | | |
|---|---|---|---|
| 3,988,304 | 10/1976 | Garsky | 260/78 A |
| 4,011,182 | 3/1977 | Sarantakis | 260/8 |
| 4,054,558 | 10/1977 | Garsky | 260/112.5 S |
| 4,187,217 | 2/1980 | Chipens et al. | 260/112.5 R |
| 4,235,886 | 11/1980 | Freidinger et al. | 424/177 |
| 4,310,518 | 1/1982 | Freidinger et al. | 424/177 |
| 5,364,851 | 11/1994 | Joran | 530/345 |
| 5,371,070 | 12/1994 | Koerber et al. | 514/9 |
| 5,618,914 | 4/1997 | Kahn | 530/317 |
| 5,670,155 | 9/1997 | Kahn | 424/208.1 |
| 5,672,681 | 9/1997 | Kahn | 530/317 |

FOREIGN PATENT DOCUMENTS

| | | |
|---|---|---|
| 0 334 244 | 9/1989 | European Pat. Off. . |
| 0 336 779 | 10/1989 | European Pat. Off. . |
| 0 370 453 | 5/1990 | European Pat. Off. . |
| 0 564 739 | 10/1993 | European Pat. Off. . |
| 2304352 | 10/1976 | France . |
| 2411828 | 7/1979 | France . |
| 41 19 544 | 10/1992 | Germany . |
| WO 89/01781 | 3/1989 | WIPO . |
| WO 92/00091 | 1/1992 | WIPO . |
| WO 92/22566 | 12/1992 | WIPO . |
| WO 93/01206 | 1/1993 | WIPO . |
| WO 94/11393 | 5/1994 | WIPO . |
| WO 95/01800 | 1/1995 | WIPO . |

OTHER PUBLICATIONS

Bell & Reisine, 1993, "Molecular biology of somatostatin receptor", *TINS* 16:34–38.

Brazeau et al, 1973, "Hypothalamic polypeptide that inhibits the secretion of immunoreactive pituitary growth hormone", *Science* 179:77–79.

Buscail et al., 1995, "Inhibition of cell proliferation by the somatostatin analogue RC–160 is mediated by somatostatin receptor subtypes SSTR2 and SSTR5 through different mechanisms", *Proc. Natl. Acad. Sci. USA* 92:1580–1584.

Byk & Gilon, 1992, "Building units for N–backbone cyclic peptides. 1. Synthesis of protected N–(ω–aminoalkylene)amino acids and their incorpration into dipeptide units", *J. Org. Chem.* 57:5687–5692.

Hruby et al., 1990, "Emerging approaches in the molecular design of receptor–selective peptide ligands: conformational, topographical and dynamic considerations", *Biochem. J.* 268:249–262.

Charpentier et al., 1989, "Synthesis and binding affinities of cyclic and related linear analogues of $CCK_8$ selective for central receptors", *J. Med. Chem.* 32:1184–1190.

Giannis & Kolter, 1993, "Peptidomimetics for receptor ligands—Discovery, development, and medical perspectives", *Angew. Chem. Int. Ed. Engl.* 32:1244–1267.

Gilon et al., 1992, "SAR studies of cycloseptide: Effects of cyclization and charge at position 6", *Chem. Biol.* Proc Am Pept Symp 12th pp. 476–477.

Gilon et al., 1991, "Backbone cyclization: A new method for conferring conformational constraint on peptides", *Biopolymers* 31:745–750.

Lamberts et al., 1990, "Somotostatin–receptor imaging in the localization of endocrine tumors", *New England J. Med.* 323:1246–1249.

(List continued on next page.)

Primary Examiner—Bennett Celsa
Assistant Examiner—Joseph W. Ricigliamo
Attorney, Agent, or Firm—Pennie & Edmonds LLP

[57] ABSTRACT

Libraries of novel backbone-cyclized peptide analogs are formed by means of bridging groups attached via the alpha nitrogens of amino acid derivatives to provide novel non-peptidic linkages. Novel building units used in the synthesis of these backbone-cyclized peptide analogs are N(((-functionalized) amino acids constructed to include a spacer and a terminal functional group. One or more of these N(((-functionalized) amino acids are incorporated into a library of peptide sequences, preferably during solid phase peptide synthesis. The reactive terminal functional groups are protected by specific protecting groups that can be selectively removed to effect either backbone-to-backbone or backbone-to-side chain cyclizations. The invention is exemplified by libraries of backbone-cyclized bradykinin analogs, somatostatin analogs, BPI analogs and Substance P analogs having biological activity. Further embodiments of the invention are Interleukin-6 receptor derived peptides having ring structures involving backbone cyclization.

24 Claims, No Drawings

OTHER PUBLICATIONS

Lamberts, 1988, "The role of somatostatin in the regulation of anterior pituitary hormone secretion and the use of its analogs in the treatment of human pituitary tumors", *Endocrine Reviews* 9:417–436.

Lymangrover & Keku, 1983, "Varying the duration of A23187 administration alters its effect on adrenal steroidogenesis", *Life Sciences* 34:371–377.

Mosberg et al., 1983, "Bis–penicillamine enkephalins possess highly improved specificity toward δ opioid receptors", *Proc. Natl. Acad. Sci. USA* 80:5871–5874.

Plotsky & Vale, 1985, "Patterns of growth hormone–releasing factor and somatostatin secretion into the hypophysial–portal circulation of the rat", *Science* 230:461–463.

Raynor et al., 1993, "Cloned somatostatin receptors: Identification of subtype–selective peptides and demonstration of high affinity binding of linear peptides", *Mol. Pharmacol.* 43:838–844.

Reisine & Bell, 1995, "Molecular biology of somatostatin receptors", *Endocrine Reviews* 16:427–442.

Reubi et al., 1995, "Multiple actions of somatostatin in neoplastic disease", *TIPS* 16:110–115.

Rizo et al., 1992, "Constrained peptides: Models of bioactive peptides and protein substructures", *Annu. Rev. Biochem.* 61:387–418.

Rodriguez et al., 1990, "Synthesis of cyclic analogues of cholecystokinin highly selective for central receptors", *Int. J. Peptide Protein Res.* 35:441–451.

Steranka et al., 1988, "Bradykinin as a pain mediator: receptors are localized to sensory neurons, and antagonists have analgesic actions", *Proc. Natl. Acad. Sci. USA* 85:3245–3249.

Veber et al., 1984, "A super active cyclic hexapeptide analog of somatostatin", *Life Sciences* 34:1371–1378.

Veber et al., 1985, "The design of metabolically–stable peptide analogs", *TINS* pp. 392–396.

R.N. Zuckerman, 1993, "The chemical synthesis of peptidomimetic libraries", *Current Opinion in Structural Biol.* 3:580–584.

G. Greiner et al., "Synthesis of New Backbone–Cyclized Bradykinin Analogs", Pept. 1994, Proc.Eur.Pept.Symp. 23rd Meeting Date 1994, 289–290.

J. Krstenansky et al., "Cyclic hexapeptide antagonists of the bradykinin $B_2$ receptor: Receptor binding and solution backbone conformation" *Letters in Peptide Science,* vol. 1 (1994) pp. 229–234.

C. Toniolo, "Conformationally restricted peptides through short–range cyclizations", Int. J. Peptide Protein Res.; vol. 35 (1990) pp. 287–300.

LIBRARIES OF BACKBONE-CYCLIZED PEPTIDOMIMETICS

CROSS-REFERENCE TO RELATED APPLICATIONS

This application is a continuation-in-part of application Ser. No. 08/444,135, filed May 18, 1995, now U.S. Pat. No. 5,723,575, which is a continuation of application Ser. No. 07/955,380, filed Oct. 1, 1992, now abandoned. This application also claims priority to Israeli patent applications 115,096 filed Aug. 29, 1996 and 99,628 filed Oct. 2, 1991.

FIELD OF THE INVENTION

This invention relates to libraries of conformationally constrained backbone cyclized peptidomimetics, to methods for the production of such libraries and to methods of using them to screen for biologically active compounds. Within the scope of this invention certain novel conformationally constrained peptidomimetic molecules which are disclosed and claimed herein.

BACKGROUND OF THE INVENTION

Peptide Libraries

Classically, the pharmaceutical industry has screened a wide variety of compounds derived from natural sources to yield potential drug candidates or lead compounds for the development of new drugs. These laborious screening efforts have relied on the random testing of a vast number of chemical entities. In recent years, various strategies have been adopted for the generation of libraries of compounds that are subsequently screened as a novel, rational approach to drug discovery and development.

It has become apparent that a variety of methodologies can be applied to the problem of generating a diverse group of candidate compounds, based on the known principles of peptide chemistry and/or molecular biology. Peptides are a convenient class of molecules for the generation of combinatorial libraries, since they are composed of a finite set of amino acid building units, which can be efficiently assembled either by chemical synthesis or transcription/translation of DNA. Combinatorial libraries are discussed by Gallop et al., *J. Med. Chem.*, 37, 1233–1251 (1994); Gordon et al., *J. Med. Chem.*, 37, 1385–1401 (1994); Pinilla et al., *Biopolymers (Peptide Science)*, 37, 221–240, (1995); and Lebl et al., *Biopolymers (Peptide Science)*, 37, 177–198 (1995). The set of amino acid building units can include only the naturally encoded amino acids, when the libraries are encoded by oligonucleotides on a plasmid, phage, or any other vector. This set can be expanded to include both D and L amino acids and/or non-natural amino acids in synthetic libraries.

Linear peptides suffer from several serious drawbacks as potential drugs, inasmuch as they are notoriously unstable in vivo, often lack high affinity of binding to their receptor, frequently lack selectivity to one kind of receptor, and generally have poor oral bioavailability. In efforts to overcome such problems, it is also possible to utilize the methodologies developed in connection with synthetic peptide libraries to generate collections of cyclic peptides, novel biopolymers and even novel branched oligomeric compounds, reviewed by Zuckermann, *Current Opinion in Structural Biology*, 3, 580–584 (1993).

One of the most significant synthetic technologies that facilitate the generation and screening of diverse chemical libraries is the resin-splitting method, which is a polymer supported multiple synthesis procedure that allows a high degree of control over the composition of a peptide mixture. Mixtures are generated by dividing a solid support into individual portions, and coupling a different amino acid to each portion, and then recombining the portions. These steps may be performed in an iterative fashion to provide the required degree of diversity.

Totally random libraries generated by these types of methods are disclosed in WO92/00091 and WO92/09300. Each individual bead will contain a unique peptide sequence, which can be probed for activity with a soluble receptor or antibody. Positive beads can be isolated and sequenced using Edman sequencing chemistry. WO92/00091 further discloses methods to provide selectively cleavable linkers between peptide and resin, such that part of the peptide can be liberated from the resin and assayed for activity in soluble form, while another part can be sequenced. In addition, it is also possible to generate random libraries in which each bead carries more than one peptide, by coupling of mixtures of amino acids to the beads, as disclosed by Hornik et al., *Reactive Polymers*, 22, 213–220 (1994).

Another methodology is disclosed by Geysen et al., *J. Immunol. Meth.*, 102, 259–274 (1987), which involves the synthesis of peptides on derivatized polystyrene pins which are arranged in such a fashion that they correspond to the arrangement of wells in a 96-well microtiter plate. Individual chemical reactions can be performed in each well, thereby yielding individual peptides on each pin. The pins are typically probed using an enzyme linked immunoassay (ELISA) or radioimmunoassay (RIA), carried out in the microtiter wells, or the peptides may be released from the pins and tested in solution. The mimotope approach of Geysen et al. generates diverse peptides that are probed for activity in situ. The best dipeptide sequence is selected for elongation to diverse tripeptides, the best tripeptide is selected for elongation to a tetrapeptide and so on.

Ideally, chemistries that are amenable to combinatorial library synthesis would have the following characteristics: be polymer-supported to facilitate the resin splitting technique; be assembled in high yield with automatable chemistry; and allow the incorporation of a wide variety of chemical functionalities.

Cyclic Peptides

Cyclic peptides are generally recognized as possessing enhanced bioavailability due to increased metabolic stability, as well as a relatively constrained conformation when compared to the same sequence in a linear form. The enhanced metabolic stability should allow diminished doses at longer intervals. The restricted conformation should improve the drug selectivity, thereby potentially preventing side-effects. All of these properties are desirable in conjunction with the quest for new drug candidates.

The generation of libraries of cyclic peptides requires, in addition to any previously stated considerations, that the cyclization reaction be performed in a high yield and with a minimum of additional manipulations. Unfortunately, classical cyclization reactions are highly sequence dependent in terms of the expected yields, making the uniform cyclization of a peptide mixture unreliable.

Recent advances in the cyclization of peptides directly on the solid support have improved the synthetic procedure, and even allowed the automation of cyclization reactions based on known cyclization schemes. In the past, cyclizations were typically performed in solution under conditions of high dilution. Polymer-supported cyclizations can both avoid potential side reactions such as oligomerization and facilitate product purification. For example, on-resin cyclization methods have recently been used to prepare cyclopeptides with bridges formed of thioethers, disulfides, or lactams between two side chains, lactams between the amino terminus and a side chain, and lactams between the amino and carboxy termini (reviewed by Zuckermann, *Current Opinion in Structural Biology*, 3, 580–584 (1993).

The use of resin-bound cyclic peptides and free cyclic peptides in combinatorial libraries is disclosed in WO 92/00091. However, these cyclic peptides do not contain any conformationally constraining element, and in cases where cyclization is achieved, these peptides may still adopt a number of conformations and suffer many of the same shortcomings as linear peptides.

Cyclic semi-random peptide libraries, which are disclosed in WO 95/01800, are exclusively cyclic penta-peptide and hexa-peptide libraries containing one or more randomized amino acids and a conformationally constraining element in the form of an amino acid residue such as proline which fixes the beta turn angles of the adjacent amino acid residues. The advantages of such conformationally constraining elements is stressed by the inventors of this approach. However, inclusion of such elements via incorporation of a particular amino acid residue into the peptide sequence may have detrimental effects on those residues required for receptor recognition or other biological activity. Furthermore, in WO 95/01800, the cyclization reaction is merely another coupling reaction in which the terminal amino group of the linear peptide is coupled to the terminal carboxy group of the peptide.

Backbone Cyclized Peptides

Backbone cyclized peptides are generally known, as discussed, for instance, in Gilon et al., *Biopolymers*, 31, 745–750 (1991) and in EPO 564,739 A2 and EPO 564,739 A3. Such compounds have not been used for constructing libraries for screening purposes.

In addition, methods are known for combining amino acids and peptides. U.S. Pat. No. 5,010,175 describes another method of incorporating random amino acids into a peptide. According to that method, a mixture of amino acids is incorporated by coupling a mixture in which the individual amino acids are present in varying proportions depending upon their relative rates of reaction in the coupling, e.g., the amount of amino acid is inversely proportional to its rate of coupling.

SUMMARY OF THE INVENTION

It is an object of this invention to provide backbone-cyclic peptide analog libraries that are suited for screening for bioactive molecules. This and other useful technology provided by the present invention is summarized below.

The present invention provides a library of chemical compounds that comprises a plurality of backbone-cyclized peptide analogs. Each compound in the library contains a peptide sequence having at least one building unit comprising an $N^\alpha$-derivative of an amino acid, and at least one backbone nitrogen in each said peptide sequence is linked to a side chain of at least one other amino acid in the peptide sequence or to at least one other backbone nitrogen in the peptide sequence by a bridging group comprising a disulfide, amide, thioether, thioester, imine, ether, or alkene bridge to form a backbone-cyclized peptide analog. At least one of the building units is preferably located other than at the end of the peptide sequence, and more preferably, none of the building units is located at the end of the peptide sequence.

According to one aspect of the invention, the library as described above comprises a plurality of backbone-cyclized peptide analogs, wherein at least one pair of backbone nitrogens in each peptide sequence is linked together to form a peptide analog having the general formula (I):

Formula (I)

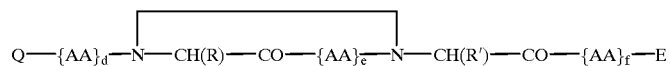

wherein: d, e, and f each independently designates 0 or an integer from 1 to 10; each {AA} designates an amino acid residue or the residue of a plurality of amino acids linked together through peptide bonding, wherein each {AA} may be the same or different; Q represents H or an acyl group; E represents a hydroxyl group, a carboxyl protecting group or an amino group, or the carboxy terminal group CO-E, wherein the CO is part of {AA}, can be reduced to $CH_2$—OH or CHO; each of R and R' is independently hydrogen or an amino acid side-chain optionally bound with a specific protecting group; and the lines designate a bridging group of the formula:

(i) -X-M-Y-W-Z-; or (ii) -X-M-Z—
wherein: M and W are independently selected from the group consisting of disulfide, amide, thioether, thioester, imine, ether, and alkene; and X, Y and Z are each independently selected from the group consisting of alkylene, substituted alkylene, arylene, homo- or hetero-cycloalkylene and substituted cycloalkylene.

In another aspect of the invention, the library comprises a plurality of backbone-cyclized peptide analogs, wherein the backbone of each analog is cyclized to a side-chain of an amino acid to form a peptide analog of the general formula (II):

Formula (II)

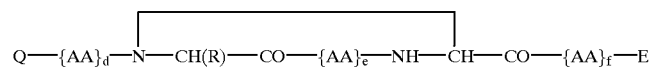

wherein the variables are as disclosed above.

A further library in accordance with the present invention comprises a plurality of backbone-cyclized bicyclic peptide analogs, each of which comprises a plurality of building units comprising an $N^\alpha$-derivative of an amino acid. Such bicyclic peptide analogs may have the formula (III):

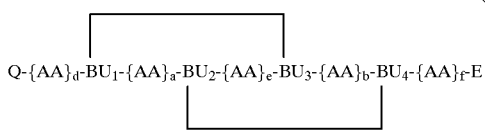

wherein each BU represents an $N^\alpha$-ω-functionalized derivative of amino acids of formula (IV):

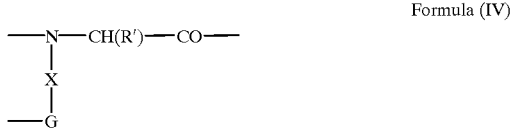

wherein X is a spacer group selected from the group consisting of alkylene, substituted alkylene, arylene, cycloalkylene and substituted cycloalkylene; R' is an amino acid side chain, optionally bound with a specific protecting group; and G is a functional group selected from the group consisting of amines, thiols, alcohols, carboxylic acids and esters, and alkyl halides; and the other variables are as disclosed above. The BU groups are incorporated into the peptide sequence and may subsequently be selectively cyclized via the functional group G with one of the side chains of the amino acids in said peptide sequence or with another ω-functionalized amino acid derivative.

It is preferred that libraries in accordance with the present invention, such as those described above, have at least four members. More preferably, at least some of the analogs are bradykinin analogs, Substance P analogs, BPI analogs, somatostatin analogs, or interleukin-6 inhibitory peptide analogs. In another preferred embodiment of the present invention, the library as described above comprises two or more sublibraries, each containing a plurality of related peptide analogs.

The present invention also provides methods for the preparation of libraries of chemical compounds as described above. The methods comprise the steps of: providing peptide sequences having a plurality of building units containing amino acids and linked nitrogen atoms and incorporating into each peptide sequence at least one $N^\alpha$-ω-functionalized derivative of an amino acid of formula (IV) by selectively cyclizing a functional group G with another ω-functionalized amino acid derivative or with one of the side chains of the amino acids in said peptide sequence to form backbone-cyclized peptide analogs.

Preferred embodiments for G in formula (IV) include amine, thiol, and carboxyl groups. Preferred embodiments for R and R' in formulas (I)–(III) include CH3—, (CH3)2CH—, (CH3)2CHCH2—, CH3CH2CH(CH3)—, CH3S(CH2)2—, HOCH2—, CH3CH(OH)—, HSCH2—, NH2C(=O)CH2—, NH2C(=O)(CH2)2—, NH2(CH2)3—, HOC(=O)CH2—, HOC(=O)(CH2)2—, NH2(CH2)4—, C(NH2)2 NH(CH2)3—, HO-phenyl-CH2—, benzyl, methylindole, and methylimidazole.

A particularly useful embodiment of the present invention involves providing the peptide sequences as described above covalently coupled to insoluble polymeric supports.

The present invention likewise provides a method of screening compounds which comprises forming a library of at least four backbone cyclized peptide analogs as described hereinabove and screening the analogs for activity as bradykinin agonists or antagonists, Substance P analogs, BPI analogs, somatostatin agonists or antagonists, or interleukin-6 inhibitory peptide analogs.

DESCRIPTION OF THE PREFERRED EMBODIMENTS

In order to fully describe the present invention, the following definitions will be used.

A "library" of backbone cyclized peptide analogs indicates a collection of peptide analogs wherein at least one conformational constraint consisting of a bridge linking novel building units via modified side chains attached to the nitrogens of the amide bonds is present. Typically the amino acids in other positions of the peptide will be "variable" or "constant". Each library is characterized by its building units, its constant amino acid residues and its variable amino acid residues. Each library may be composed of "sub-libraries" which are synthesized in parallel, using a divergent or convergent synthetic scheme.

A "variable" position or amino acid residue may have more than one amino acid in the specified position of the peptide. Typically, in a set of sub-libraries, each sub-library differs from the other in the identity of at least one of its defined amino acid(s) (e.g., the defined amino acid(s) will be constant throughout a single sub-library, yet differ between sub-libraries within the set). A "constant" amino acid or sequence is one whose identity and position are invariant throughout the peptides of the library, and across a set of sub-libraries.

The conformation of a peptide backbone is determined by the three dihedral angles φ (C-N-Cα-C), ψ (N-Cα-C-N) and ω (Cα-C-N-Cα), which not only specify the position of the peptide backbone atoms, but also the angle of projection of the amino acid side chains (Ca–Cb vector) from the peptide backbone. A peptide with a "conformationally constrained backbone" will either be rigid, existing in only a single conformer characterized by specific values of φ, ψ, and ω for each residue, or will exist as an equilibrium mixture of a relatively few discrete conformers, the backbone torsional angles of all residues for each conformer being well described. Thus, a backbone-cyclic peptide with a conformational constraint indicates one in which the atoms and bonds which constitute the ring are energetically able to assume only a limited number of positions in space relative to one another at or around room temperature, and these positions may be well defined by conventional techniques of molecular modeling and crystallography.

An "optimized" conformer is that which has the greatest activity (e.g., biological response, binding or inhibition of biological response or binding) when a library having a defined amino acid sequence is screened for a given target activity. Preferably, only a single bridge will confer optimal activity. An optimized bridge is characterized by its chemical structure and position in the peptide sequence The "amino acid set" comprises all amino acids which are to be varied within the peptide at a particular position. Typically the amino acid set will comprise 2–50 different amino acid residues. The amino acid set may be varied in the number of amino acid residues and types of residues for each position in the peptide, or the same set may by used for all positions in the peptide.

The term "amino acid" refers to compounds which have an amino terminus and carboxy terminus, preferably in a 1,2-1,3-, or 1,4-substitution pattern on a carbon backbone. α-Amino acids are most preferred, and include the 20 natural amino acids (which are L-amino acids except for glycine), which are found in proteins, the corresponding D-amino acids, the biosynthetically available amino acids which are not found in proteins (e.g., 4-hydroxy-proline, 5-hydroxy-lysine, citrulline, ornithine, canavanine, djenkolic acid, β-cyanolanine), and synthetically derived α-amino acids, such as amino-isobutyric acid, norleucine, norvaline, homocysteine and homoserine. β-Alanine and γ-aminobutyric acid are examples of 1,3- and 1,4-amino acids, and many others are well known to the art. Statine-like isosteres (a dipeptide comprising two amino acids wherein the CONH linkage is replaced by a CHOH), hydroxyethylene isosteres (a dipeptide comprising two amino acids wherein the CONH linkage is replaced by a $CHOHCH_2$), reduced amide isosteres (a dipeptide comprising two amino acids wherein the CONH linkage is replaced by a $CH_2NH$ linkage) and thioamide isosteres (a dipeptide comprising two amino acids wherein the CONH linkage is replaced by a CSNH linkage) are also useful residues for this invention.

As used herein "peptide" indicates a sequence of amino acids linked by peptide bonds. The peptide analogs of this invention comprise a sequence of amino acids of 4 to 12 amino acid residues, preferably 6 to 10 residues, each residue being characterized by having an amino and a carboxy terminus.

A "building unit" indicates an $N^\alpha$-derivatized α-amino acid of the general Formula IV:

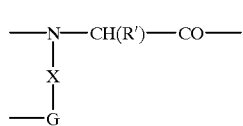

Formula (IV)

wherein X is a spacer group selected from the group consisting of alkylene, substituted alkylene, arylene, cycloalkylene and substituted cycloalkylene; R' is an amino acid side chain, optionally bound with a specific protecting group; and G is a functional group selected from the group consisting of amines, thiols, alcohols, carboxylic acids and esters, and alkyl halides; which is incorporated into the peptide sequence and subsequently selectively cyclized via the functional group G with one of the side chains of the amino acids in said peptide sequence or with another w-functionalized amino acid derivative.

The methodology for producing the building units is described in international patent application PCT/IB95/00455, which is incorporated in its entirety by way of reference. The building units are abbreviated by the three letter code of the corresponding modified amino acid followed by the type of reactive group (N for amine, C for carboxyl), and an indication of the number of spacing methylene groups. For example, Gly-C2 describes a modified Gly residue with a carboxyl reactive group and two methylene spacer, and Phe-N3 designates a modified phenylalanine group with a amino reactive group and three methylene spacer.

As used herein "linear peptide" denotes the peptide sequence that is constructed only of amino acid residues and is devoid of any building units.

As used herein "backbone cyclic peptide" denotes an analog of a linear peptide which contains at least one building unit that has been linked to form a bridge via the alpha nitrogen of the peptide backbone to another building unit, or to another amino acid in the sequence.

As used herein "pre-cyclic peptide" denotes an analog identical to the cyclic analog except that it is retained in the non-cyclized form to serve as control during the biological or other screening assays.

"Pre-cyclic peptide library" denotes the portion of the peptide analog library, containing the building units identical to those of the backbone cyclized library, but is devoid of the conformational constraint of the latter.

Certain abbreviations are used herein to describe this invention and the manner of making and using it. For instance, AcOH refers to acetic acid, Ada refers to adamantanacetyl, Adac refers to adamantanecarbonyl, Alloc refer to allyloxycarbonyl, BCIP refers to 5-bromo-4-chloro-3-indolyl phosphate, BK refers to bradykinin, Boc refers to the t-butyloxycarbonyl radical, BOP refers to benzotriazol-1-yloxy-tris-(dimethylamino)phosphonium hexafluorophosphate, BPI refers to Bactericidal/permeability increasing protein, BSA refers to bovine serum albumin, Cbz refers to the carbobenzyloxy radical, DCC refers to dicyclohexylcarbodiimide, DCM refers to Dichloromethane, Dde refers to 1-(4,4-dimethyl2,6-dioxocyclohex-1-ylidene-ethyl, DIEA refers to diisopropylethyl amine, DMF refers to dimethyl formamide, DPPA refers to diphenylphosphoryl azide, Dtc refers to 5,5-dimethylthiazolidine-4-carboxylic acid, EDC refers to N-ethyl-N' (dimethylaminopropyl)-carbodiimide, EDT refers to ethanedithiol, Fmoc refers to the fluorenylmethoxycarbonyl radical, GPI refers to guinea pig ileum, HATU refers to [O-(7-azabenzotriazol-1-yl)-1,1,3,3-tetramethyl uronium hexafluorophosphate, HBTU refers to 1-hydroxybenztriazolyltetramethyl-uronium hexafluorophosphate, HF refers to hydrofluoric acid, HOBT refers to 1-hydroxybenzotriazole, HPLC refers to high pressure liquid chromatography, IL-6 refers to interleukin 6, IL-6R refers to interleukin 6 receptor, MALDI-TOF MS refers to matrix-assisted laser desorption, time-of-flight mass spectrometry, Mts refers to the 4-methoxy-2,3,6-trimethylbenzenzsulfonyl, NBT refers to nitro blue tetrazolium, NMM refers to N-methylmorpholine, NMP refers to 1-methyl-2-pyrolidonone, PBS refers to Phosphate buffered saline, Pmc refers to pentamethylchroman-6-sulfonyl, PNPP refers to p-nitrophenyl phosphate, PPA refers to 1-propanephosphoric acid cyclic anhydride, PyBOP refers to Benzotriazole-1-yl-oxy-tris-pyrrolidino-phosphonium hexafluorophosphate, PyBrOP refers to Bromo-tris-pyrrolidino-phosphonium hexafluorophosphate, RT refers to room temperature, SMPS refers to simultaneous multiple peptide synthesis, SP refers to Substance P, SRIF refers to Somatotropin Release Inhibitory Factor, TBTU refers to 2-(1H-benzotriazole-1-yl)-1,1,3,3-tetramethyluronium tetrafluoroborate, t-Bu refers to the tertiary butyl radical, TFA refers to trifluoroacetic acid, TIS refers to triisopropylsilane, Tpr refers to thiazolidine-4-carboxylic acid, Trt refers to trityl, Ts refers to toluenesulfonyl.

The amino acids used in this invention are those which are available commercially or are available by routine synthetic methods. Certain residues may require special methods for incorporation into the peptide, and either sequential, divergent and convergent synthetic approaches to the peptide sequence are useful in this invention. Natural coded amino acids and their derivatives are represented by three-letter codes according to IUPAC conventions. When there is no indication, the L isomer was used. The D isomers are indicated by "D" before the residue abbreviation. List of Non-coded amino acids: Abu refers to 2-aminobutyric acid, Aib refers to 2-amino-isobutyric acid, Cha refers to cyclohexylalanine, Hcys refer to homocysteine, Hyp refers to S-trans-4-hydroxyproline, 1Nal refers to 1-naphtylalanine, 2Nal refers to 2-naphtylalanine, Nva refers to norvaline, Oic refers to octahydroindolecarboxylic acid, Phg refers to phenylglycine, pClPhe refers to p-chloro-phenylalanine, pFPhe refers to p-fluoro-phenylalanine, pNO2Phe refers to p-nitro-phenylalanine, Thi refers to thienylalanine.

Methodology

According to the present invention, the principles of cyclic peptide libraries have now been successfully applied to the generation of novel mixtures of peptidomimetic compounds, which are characterized in that they incorporate novel building units with modified side chains attached to the alpha nitrogens of alpha amino acids. These novel building units permit the generation of peptidomimetics, that are backbone-to-backbone cyclized and conformationally constrained.

The most striking advantages of this approach are as follows:

1) The method enables cyclization of the peptide sequence without compromising the side chains of the peptide sequence that are involved in biological recognition and functionality. 2) The method allows optimization of the peptide conformation by allowing permutation of the bridge length, direction, and bond type (e.g., amide, disulfide, thioether, thioester, etc.) and position of the bond in the ring. 3) When applied to cyclization of linear peptides of known activity, the bridge is expected not to be involved in target recognition, thereby creating a site suitable for attachment of tags such as radioactive tracers, cytotoxic drugs, light capturing substances, or any other desired label.

The newly generated libraries, disclosed according to the present invention, now enable screening for varying degrees of conformational constraint, in order to find the optimal backbone conformation of the peptide in performing its role as an agonist or antagonist. This is accomplished by varying both the position of the bridgeheads (i.e., the positions in the linear sequence of residues that are to be cyclized), as well as varying the length, the direction and the bond type of the bridge between these units.

The general methodology for preparing the cyclic peptides of this invention involves solid phase peptide synthesis using an orthogonal protection scheme which allows for chain elongation, selective removal of the protecting groups, cyclization of the protected peptides and removal of all side-chains protecting groups with or without cleavage from the resin. It is desirable that the various peptide sequences be present in the libraries in substantially equal amount.

The coupling reactions are performed by methods to create amide or ester bonds and are performed by methods familiar in the art as described herein. Typical coupling reagents are carbodiimides, activated anhydrides and esters and acyl halides. Reagents such as EDC, DCC, DPPA, PPA, BOP, PyBOP, PyBrop, HATU, HBTU, TBTU, HOBT, N-hydroxysuccinimide and oxalyl chloride are typical.

Synthesis of peptide libraries containing more than one building unit, bridge type or amino acid at one or more positions can be performed by different synthetic schemes, as known in the art of peptide synthesis. Preferred methods of generating libraries include the following:

A. Partitioning, Coupling, and Recombination Scheme

1. The resin is partitioned into a number of aliquots corresponding to the number of amino acids or building units used for the defined set used at each position.

2. Each aliquot is coupled exhaustively to a single building unit or amino acid using solid phase methodologies.

3. The synthesis subsequently proceeds by recombining of all resin portions before the next coupling step is performed.

4. Steps 1 and 2 may be repeated as necessary, depending on whether a constant or variable residue is being coupled.

Alternatively, in a divergent synthetic scheme, at any given point in the synthesis each resin aliquot may be treated individually from that point on until the end of the synthesis, thus generating sub-libraries. The synthesis may be carried out in parallel for part or all of the remaining synthetic process, up to and including the cyclization and cleavage steps.

B. Coupling of Mixtures

Synthesis is performed using a mixture of amino acids that are coupled in a certain position to one resin aliquot. The use of exactly one equivalent of total amino acid and the long coupling time serves partially to correct for the different rates of coupling of the individual amino acids in the mixture and to help ensure that an equimolar mixture of amino acids is obtained at each position. The procedure of U.S. Pat. No. 5,010,175 can also be used.

After completion of the solid phase peptide elongation, by any scheme, portions of the peptide are cyclized, via the bridging groups attached to the backbone amide bond nitrogens of the building units. It is preferable that a portion is retained in the non-cyclized form to serve as control during the biological or other screening assays. This portion of the peptide analog library, which contains the building units identical to those of the backbone cyclized library, but is devoid of the conformational constraint of the latter, is referred to as the "pre-cyclic". Alternatively, in any of the synthesis schemes, the backbone cyclization step may be performed and additional coupling cycles of amino acid residues may then be carried out.

Portions of the peptide may be cleaved from the resin and protecting groups removed, as required prior to assay of biological activity. The peptides are cleaved from the resin support by methods known in the art, the precise method being dependent upon the characteristics of the resin. It will be understood by those skilled in the art that the removal of certain protecting groups may occur simultaneously with cleavage of the peptide from the resin.

Typically the coupling between the resin and the first amino acid will form an ester bond, which will yield a carboxylic acid group on the peptide when it is cleaved from the resin. HMPB, Rink, PAM, Hycram and hydroxymethyl resins are exemplary. In addition, the carboxy terminal amino acid group may be converted to an amide, an ester or reduced to a terminal alcohol.

The reactive functional groups of the side chains of each amino acid or peptide are suitably protected as known in the peptide art. For example, the Boc, Cbz or Fmoc group may be used for protection of an amino group, especially an α-amino group. An alkyl (e.g., t-Bu, Me), cHex, benzyl or allyl ester may be used for the protection of the side chain carboxyl of Asp or Glu. A benzyl, or suitably substituted benzyl, trityl, Alloc or t-Bu group is used to protect the mercapto group of cysteine, or other thiol containing residues; or the hydroxyl of Tyr, Ser or Thr. Cys and other sulfur-containing amino acids may also be protected by the Acm group or by formation of a disulfide with a thioalkyl (e.g., ethyl mercaptan) or thioaryl group. The benzyl/benzyloxymethyl, or a suitably substituted benzyl/benzyloxymethyl, Boc or formyl group may be used for protection of the imidazolyl group of His; and the Pmc, nitro or a suitably substituted benzene-sulfonyl group (e.g., Ts, Mts) for protection of the guanidino nitrogen of Arg. The phthalamido, Boc, Fmoc, Alloc carbobenzyloxy or benzyl group, or suitably substituted benzyl or benzyloxy group, may be used for protecting the (-amino group of lysine. Suitable substitution of the carbobenzyloxy or benzyl protecting groups is substitution with one to five chloro, bromo, nitro, methoxy or methyl groups, usually ortho and/or para, and is used to modify the reactivity of the protective group. These protective groups are removed by such methods as catalytic hydrogenation, sodium in liquid ammonia, hydrazine, base, TFA or HF treatment, as known in the art. The choice of side chain protecting groups is chosen so that they will not be removed under conditions which are used to deprotect the reactive functional group used in the coupling reaction (e.g., generally the (-amino group) to form the peptide backbone of the peptide chain. The protective group of the reactive functional group is removed prior to coupling each successive amino acid.

The bridging groups of the building units (i.e., G in Formula IV) are used according to the present invention with an orthogonal protection scheme, such that these protecting groups can be removed selectively, under conditions which do not affect the protecting groups on the side chains or cleavage of the peptide from the resin. This enables backbone cyclization on the resin, which is preferred synthetically. Alternatively, the fully protected peptide may be removed from the resin, and cyclization performed in solution after selective removal of the protecting groups of the building units.

The cyclization reaction is carried out by means of selective coupling the bridging group of one building unit to a bridging group of another building unit or amino acid side chain. By way of example, the PyBOP is particularly useful reagent for conducting the coupling reaction, in case of formation of an amide bond. To form a disulfide bridge oxidative conditions are used.

A typical scheme for preparing libraries according to the invention involves using resin such as TentaGel or Rink resin as the support, Fmoc as the (-amino protecting group, t-butyl based protecting groups for the side chains, and allyl/Alloc for the side chain of building unit. Other schemes of orthogonal protection known to those skilled in the art are obviously applicable as well. Generally, one will calculate the number of amino acids in the amino acid set for each position in the peptide, and will use sufficient resin so that there is at least a five-fold molecular excess of reactive sites on the resin to the number of possible peptide sequences.

When the C-terminal amino acid is variable, it is convenient to begin the synthesis using a mixture of individual aminoacyl peptide resins with an equimolar distribution of the amino acids used. An equimolar mixture of the same protected amino acids can also be prepared. An aliquot of the protected amino acid mixture corresponding to exactly one equivalent of total amino acid is allowed to couple to the resin mixture. The use of exactly one equivalent of total amino acid and the long coupling time serves partially to correct for the different rates of coupling of the individual amino acids in the mixture and to help ensure that an equimolar mixture of amino acids is obtained at each position. At this point, a Kaiser test may be performed to assess the completeness of coupling and recoupling with one equivalent of the equimolar mixture can be performed as necessary.

In a most preferred embodiment according to the present: invention, the amino acid sequence scaffold is based on known active sequences from natural or synthetic peptides or proteins (e.g. Somatostatin, Bactericidal/Permeability Increasing protein, Interleukin-6 or Interleukin-6 Receptor, Substance P or Bradykinin). It will thus be possible to further improve the activity of such known sequences, upon rigidification of the active conformer. In other instances, it will be possible to further improve the activity of other types of peptidomimetics, not involving backbone cyclizations (e.g. Polymixins).

The application of the present invention is particularly suitable for peptides of 3 up to 14 amino acid residues. However, it is also useful to define peptide fragments that compete with larger polypeptides having up to 45 to 70 residues. These methods can be used to produce both conformationally constrained agonists and antagonists. They can either optimize the properties of known sequences or generate novel analogs.

Amino acids in certain positions are replaced by Backbone-Cyclization Building-Units or by natural and non-natural trifunctional amino acids such as Asp, Glu, Cys, Hcys, Lys, Orn and their D counterparts. Thus positional as well as structural scans are performed by changing the position of cyclization, the link of the ring to the backbone, the chirality at the position of cyclization, the ring forming bond, the ring size and the exact placement of the bond within the ring. These variations may also be performed in conjunction with changing the amino acids sequence of the peptide.

In one preferred embodiment of the present invention, backbone-cyclic peptide libraries were prepared by Simultaneous Multiple Peptide Synthesis (SMPS, Houghten, Proc. Natl. Acad. Sci. USA 82, 5131–5135, 1985). Resin portions were kept separate by capturing them in polypropylene bags, and coupling and deprotection cycles were performed on all bags together in a polypropylene box, except for steps of coupling of different amino acids at the same sites of the peptides. In each bag there was only one (crude.) compound by the end of the synthesis.

After completion of the synthesis, samples of resin-peptide were taken form each bag to make mixtures based on structural homology (e.g. a mixture could be comprised of all peptides with a D-amino acid at a certain position or all peptides with the same ring size etc.). The peptides were cleaved from the resin and screened for biological activity as crude mixtures. Then peptides from the most active mixtures were cleaved separately from the resin, purified by preparative HPLC, characterized by mass-spectrometry and amino-acid-analysis and assayed for their biological activity.

Backbone-cyclic peptides containing a disulfide bond in the ring were prepared by inclusion of protected ω-thiol building units in the sequence. Backbone to backbone cyclization was performed by disulfide bond formation between two such building units in a given sequence. Alternatively were backbone to side-chain cyclic peptides prepared by closing a disulfide ring between the w-thiol group of a building unit and the thiol group of Cys or HCys. Formation of the disulfide bond on the resin was obtained by adaptation of the diphenylsulfoxide-silyl chloride method (Akaji et. al. J. Amer. Chem. Soc., 114, 4137, 1992). This is done as was presented in the literature (Camarero et. al., Tetrahedron Lett., 36, 1137–1140, 1995) for prolonged periods (16–24 h) at room temperature. The yields were not high but were sufficient for biological screening. A backbone-bicyclic peptide library was prepared by combining lactam and disulfide cyclizations. Analogs of [Arg6]SP6-11 where Met11 was replaced by an w-thiol containing building unit, Cys or HCys, and Gly9 was replaced by an w-amine building unit were synthesized manually in SMPS bags using Fmoc chemistry. The w-amino group of the building unit in position 9 was protected by Boc. After coupling of this building unit the Boc group was removed and to the w-amine was coupled a second w-thiol building unit or amino acid with its a-amine protected with Boc. Then the Fmoc group was removed from the a-amine of the building unit in position 9 and the synthesis of the peptides was continued. After completion of the synthesis of the hexapeptide chain, a dicarboxylic acid was coupled to the amino terminus and then the Boc group protecting the α-amino group of the ω-thiol containing building unit or amino acid was removed and the lactam ring was closed. Then the disulfide ring was closed by the above mentioned solid-phase diphenylsulfoxide-silyl chloride method. Since the yields of these peptides were relatively low due to side-reactions in the disulfide formation step, the peptides comprising the most active mixtures were resynthesized and cyclized separately after cleavage from the resin by the normal solution diphenylsulfoxide-silyl chloride method.

In another preferred embodiment, libraries are synthesized by the portioning-mixing method (Furka et al. Int. J. Pep. Protein Res. 37, 487–493, 1991). Typically, in each variable position the resin is split into the appropriate number of aliquots, and different amino acids or building units are coupled to each. Any appropriate reaction vessel may be used to contain these aliquots; in a preferred embodiment it is very convenient to use an individual column for each portion of the resin. After the coupling is completed and the coupling mixture is washed out, all or part of the resin portions are recombined. Removal of α-N protecting groups (typically Fmoc) is performed on the recombined resin. Further cycles of coupling, and the other steps, are carried out similarly with or without portioning and mixing of the resin. Preferably, in this scheme of production, the library consists of several sub-libraries which differ in one or more amino acid residue, building unit and/or bridge. The final resin portions (sub-libraries) are cyclized to yield backbone cyclized mixtures or left as pre-cyclic mixtures. After removal of side-chain protecting groups and optional cleavage of the sub-library peptides from the resin, screening of the sub-libraries set leads to identification of an optimized sub-library. Further synthesis and screening cycles lead to the optimized backbone cyclized peptide. In each successive synthetic cycles, the complexity of the mixture is smaller.

In another preferred embodiment libraries are synthesized on non-cleavable resins to yield solid-phase supported libraries. Diversity of bridges and amino acids sequence is achieved by the positional scanning method (reviewed by Pinilla et. al. ibid.).

EXAMPLES

Conformationally constrained peptidomimetic libraries have been constructed based on the sequences of a number of known biologically active peptides. The following peptides serve as examples that are intended to illustrate how to make and use the libraries and methods of this invention and are in no way to be construed as a limitation.

General Synthesis of Libraries of Somatostatin Analogs, BPI Analogs and Interleukin-6 Inhibitory Peptide Analogs The libraries were synthesized on TentaGel amide Resin (substitution level of 0.2–0.3 mmol/g) using conventional solid-phase peptide synthesis (known to those skilled in the art). In most cased NMP was used as a solvent, DMF in few cases. Synthesis scale was 0.2–2 (mole for each peptide in library or sub-library. Unless mentioned, all reactions were performed at room temperature.

In each coupling step where more then one amino acid had to be coupled, the resin was divided into the appropriate number of portions and different amino acid was added to each portion.

Coupling was performed, twice for each position with 3 molar excess of each amino acid, 3 molar excess of PyBrop and 6 molar excess of DIEA for duration of 1–16 hours. All amino acids were protected with FMOC in their (-amine.

Side-chain protections were as follow: His(Trt); Lys(Boc or Dde); Orn(Boc); Ser(tBu); Thr(tBu); Tyr(tBu).

After double coupling, the resin portions were washed, recombined and FMOC deprotection was performed using 20% piperidine in NMP for total of 20–40 minutes. After additional washes the resin was divided again (if necessary) for the coupling of the next amino acid/s.

Before cyclization, the Allyl/Alloc protection of the amine and carboxyl of the building units were removed by treatment with a solution of 2 mole equivalents (one for each Allyl/Alloc molecule in peptide), of Pd(PPh3)4 dissolved in chloroform containing 2.5% AcOH and 5% NMM for 2–2.5 hours or twice for 1 hour, resins were washed with the above solvent without the palladium before and after treatment, additional washes with NMP were made at the end of the removal process.

For cases were the backbone-cyclic library and the pre-cyclic libraries are synthesized simultaneously, the resin was divided into separate portions before cyclization and cyclization was performed only for the "cyclic library" portion. The corresponding linear library was synthesized separately because it contains non-modified amino acids instead of the building units. Cyclization was performed twice or three times, each with 3 molar excess of PyBOP and 6 molar excess of DIEA for 2–16 hours with NMP washes between and after coupling.

The peptides were cleaved from the resin portions after washes with DCM, by double treatment with TFA 70%, H2O 5%, TIS 1%, EDT 2.5%, DCM (mixture A) or TFA 70%, H2O 5%, TIS 1%, Phenol 5%, DCM (mixture B) or 60% TFA, 10% H2O and 30% DCM (mixture C) plus additional wash with neat TFA. The three cleavage solutions of each resin portion were collected together, evaporated with nitrogen stream, 0.5–1 ml of H2O were added to each sample that was then freeze-dried. The peptide mixtures were then partially purified on C-18 SEP-PAK (Millipore Corp.) using 0.1% acetic acid or TFA in H2O as buffer A and 50–80% CH3CN in 0.1% acetic acid/H2O as buffer B and freeze-dried.

Yields of semi-purified peptide mixtures were generally 10–60% of initial synthesis scale. Optimization of synthetic procedures during scale-up will lead to higher yields.

Each sub-library synthesized was characterized by mass spectrometry (MALDI-TOF MS), and amino acid analysis.

The building units are abbreviated by the three letter code of the corresponding modified amino acid followed by the type of reactive group (N for amine, C for carboxyl), and an indication of the number of spacing methylene groups. For example, Gly-C2 describes a modified Gly residue with a carboxyl reactive group and two methylene spacer, and Phe-N3 designates a modified phenylalanine group with a amino reactive group and three methylene spacer.

General Screening of Libraries of Somatostatin Analogs, BPI Analogs and Interleukin-6 Inhibitory Peptide Analogs:

Somatostatin libraries synthesized in these schemes are typically tested in-vitro for their inhibition of the natural peptide (SRIF-14) binding to its 7-transmembranal receptors, for their influence on second messengers and cell growth and in-vivo for inhibition on hormones and enzymes secretion. BPI libraries synthesized in these schemes are tested for their inhibition of fungi growth. IL-6 libraries are tested for their influence on the native protein (IL-6) binding to its transmembranal receptors (IL-6R and gp130) and for inhibitory activity on IL-6 action. Both libraries synthesized in these schemes are tested for their in-vitro and in-vivo metabolic stability.

Metabolic Stability Tests as Parameter for Selection:

Libraries are tested for their stability to enzymatic degradation by incubation in serum or in tissue homogenate, separation of the proteins and recording of the peptide peaks by HPLC before and after incubation. The peptide peaks that are not changed with increased incubation time are most stable for degradation. These peaks are separated and characterized by mass spectrometry, N-terminal sequence and comparison to purified peptide peaks. In this way the most stable peptides from library or sub-library are rapidly identified.

General Synthesis of Bradykinin and Substance P Analogs

Libraries were synthesized on such resins as hydroxybenzyl resin with 0.39 meq/gr substitution level (BK libraries) or on 4-methylbenzhydrylamine resin with 0.57 meq/gr substitution level (SP libraries) using "tea-bag" simultaneous multiple peptide synthesis (Houghten, Proc. Natl. Acad. Sci. USA 82:5131–5135, 1985). Usual solvents for peptide synthesis such as NMP or DMF were used. Synthesis scales were 20–60 mmole for each peptide. All reactions were performed at room temperature.

Coupling was performed with 6 molar excess of each amino acid, 6 molar excess of coupling agent and 12 molar excess of DIEA. for duration of 2–3 hours. Coupling agents were HBTU for normal Fmoc/Boc-amino acids couplings, PyBroP for couplings of and building units and TBTU for lactam ring cyclization. Couplings to building units and lactam ring cyclizations were repeated 3–4 times. Amino acids were protected with Boc or Fmoc on the a-amine. Side-chain protections were as follow: Arg(Tos), D-Arg(Tos), Hyp(Bzl), Glu(tBu), D-Glu(t-Bu), D-Asp(t-Bu), Ser (Bzl). Boc, t-butyl and benzyl were used for the protection of the w-amino, carboxyl and sulfhydryl groups of the building unit.

Fmoc deprotection was performed with 20% piperidine in DMF for 30 minutes once or twice. After the completion of peptide elongation, the Boc and t-Bu protecting groups were removed with 55% TFA in DCM—once for 2 min and a second time for 30 min.

In cases where the cyclic and pre-cyclic peptides were synthesized simultaneously, the resin was divided into two separate portions before cyclization, and cyclization was performed only on the "cyclic library" portion using 6 fold excess of TBTU and 12 fold excess of DIEA. Cyclization was repeated until negative Kaiser test. The corresponding pre-cyclic library was either left intact, or the amine and carboxyl groups were blocked by acetylation and reaction with methylamine respectively. Acetylation was performed with 10 molar excess of acetic anhydride in DMF or NMP and 1 equivalent of DMAP as catalyst. Reaction with methylamine was carried out by activation of the free carboxylic group for 30 min with 10 molar excess of DIC (0.5M in DCM) and HOBT (0.5M in DMF) followed by addition of 10 molar excess of 10M solution of methylamine in ethanol.

Peptide-resin mixtures based on structural homology were prepared using samples from each tea-bag. They were cleaved from the resin using HF/anisole at 0–5° C. and screened for biological activity as crude mixtures.

Screening of Bradykinin and Substance P Libraries for Biological Activity:

Bradykinin and Substance P backbone cyclized libraries synthesized in these schemes, are typically tested for their agonist or antagonist activity on Guinea Pig Ileum (GPI) contraction (Sawutz et. al. PNAS. 91, 4693–4697 1994).

BRADYKININ ANALOGS:

Example 1 cyclo[—(CH2)n—NH—CO—(CH2)k—NH—CO—(CH2)m—CO-D-Arg-Arg-Pro-Hyp-Gly-Phe-Ser-D-Phe-N-]—CH2—CO-Arg-OH and pre-cyclic analogs.

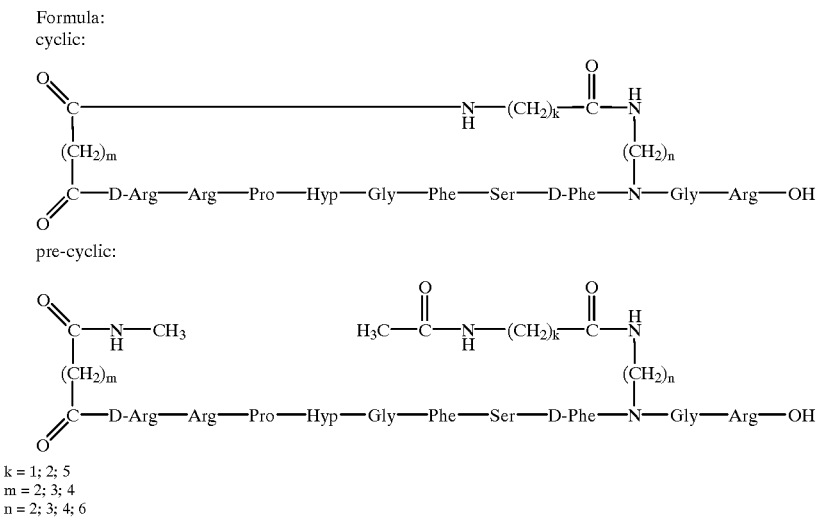

| CYCLIC PEPTIDES | | | | | |
|---|---|---|---|---|---|
| Peptide number | k | m | m | ring size | Mass (calc.) | Mass (obs.) |
| 201 | 0 | 2 | 2 | 32 | 1317.4 | 1317 |
| 202 | 0 | 3 | 2 | 33 | 1331.4 | 1331 |
| 203 | 0 | 4 | 2 | 34 | 1345.4 | 1345 |

-continued

CYCLIC PEPTIDES

| Peptide number | k | m | m | ring size | Mass (calc.) | Mass (obs.) |
|---|---|---|---|---|---|---|
| 204 | 0 | 4 | 3 | 35 | 1359.5 | 1359 |
| 205 | 0 | 4 | 4 | 36 | 1373.5 | 1373 |
| 206 | 0 | 3 | 6 | 37 | 1387.5 | 1387 |
| 207 | 0 | 4 | 6 | 38 | 1401.6 | 1401 |
| 208 | 1 | 4 | 4 | 39 | 1430.6 | 1429 |
| 209 | 1 | 3 | 6 | 40 | 1444.6 | 1444 |
| 210 | 1 | 4 | 6 | 41 | 1458.6 | 1458 |
| 211 | 2 | 4 | 6 | 42 | 1472.7 | 1471 |
| 212 | 5 | 2 | 6 | 43 | 1486.7 | 1485 |
| 213 | 5 | 3 | 6 | 44 | 1500.7 | 1500 |

No biological activity of this mixture has been found.

PRECYCLIC PEPTIDES

| Peptide number | k | m | m | Mass (calc.) | Mass (obs.) |
|---|---|---|---|---|---|
| 214 | 0 | 2 | 2 | 1389.5 | 1390 |
| 215 | 0 | 3 | 2 | 1403.5 | 1403 |
| 216 | 0 | 4 | 2 | 1417.5 | 1417 |
| 217 | 0 | 4 | 3 | 1431.5 | 1432 |
| 218 | 0 | 4 | 4 | 1445.6 | 1446 |
| 219 | 0 | 3 | 6 | 1459.6 | 1460 |
| 220 | 0 | 4 | 6 | 1473.6 | 1474 |
| 221 | 1 | 4 | 4 | 1502.6 | 1502 |
| 222 | 1 | 3 | 6 | 1516.6 | 1516 |
| 223 | 1 | 4 | 6 | 1530.6 | 1529 |
| 224 | 2 | 4 | 6 | 1544.7 | 1544 |
| 225 | 5 | 2 | 6 | 1558.7 | 1558 |
| 226 | 5 | 3 | 6 | 1572.7 | 1571 |

No biological activity of this mixture has been found.

Example 2

Ada-D-Arg-Arg-cyclo[—(CH2)n—NH—CO—(CH2)k—NH—CO—(CH2)m—CO—N—CH2—CO-Hyp-Gly-Leu-N-]—CH2—CO-D-Phe-Leu-Arg—OH and pre-cyclic analogs.

Formula:

CYCLIC PEPTIDES

| Peptide number | k | m | n | ring size |
|---|---|---|---|---|
| 253 | 0 | 2 | 2 | 19 |
| 254 | 0 | 2 | 3 | 20 |
| 255 | 0 | 3 | 3 | 21 |
| 256 | 0 | 3 | 4 | 22 |
| 257 | 0 | 2 | 6 | 23 |
| 258 | 0 | 3 | 6 | 24 |
| 259 | 2 | 3 | 3 | 25 |
| 260 | 2 | 3 | 4 | 26 |
| 261 | 2 | 2 | 6 | 27 |
| 262 | 2 | 3 | 6 | 28 |
| 263 | 5 | 3 | 4 | 29 |
| 264 | 5 | 2 | 6 | 30 |
| 265 | 5 | 3 | 6 | 31 |

$K_d$ (mixture) = $9.5 \times 10^{-5}$ M

PRECYCLIC PEPTIDES

| Peptide number | k | m | n |
|---|---|---|---|
| 266 | 0 | 2 | 2 |
| 267 | 0 | 2 | 3 |
| 268 | 0 | 3 | 3 |
| 269 | 0 | 3 | 4 |
| 270 | 0 | 2 | 6 |
| 271 | 0 | 3 | 6 |
| 272 | 2 | 3 | 3 |
| 273 | 2 | 3 | 4 |
| 274 | 2 | 2 | 6 |
| 275 | 2 | 3 | 6 |
| 276 | 5 | 3 | 4 |
| 277 | 5 | 2 | 6 |
| 278 | 5 | 3 | 6 |

48% inhibition (mixture) at $10^{-5}$ M

Example 3

H-D-Arg-Arg-cyclo[—(CH2)n—NH—CO—(CH2)k—NH—CO—(CH2)m—CO—N—CH2—CO-Hyp-Gly-Leu-N-]—CH2—CO-D-Phe-Leu-Arg-OH and pre-cyclic analogs.

cyclic:

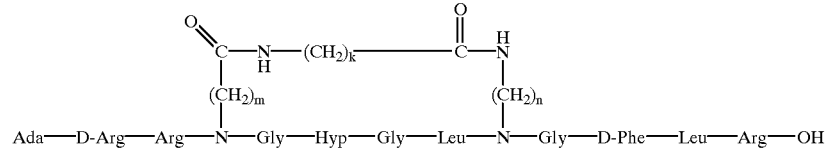

precyclic:

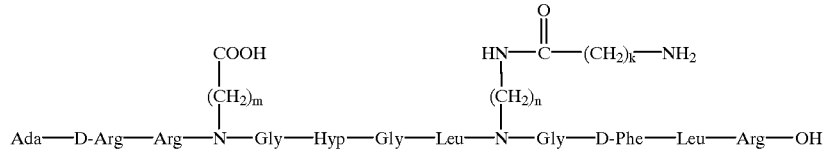

k = 2; 5
m = 2; 3
n = 2; 3; 4; 6

Formula:
cyclic:

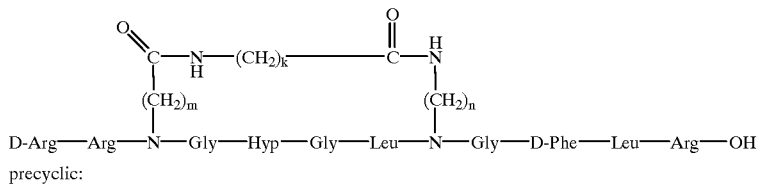

D-Arg—Arg—N—Gly—Hyp—Gly—Leu—N—Gly—D-Phe—Leu—Arg—OH precyclic:

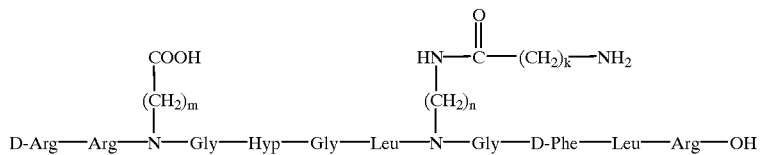

D-Arg—Arg—N—Gly—Hyp—Gly—Leu—N—Gly—D-Phe—Leu—Arg—OH k = 2; 5
m = 2; 3
n = 2; 3; 4; 6

Example 4

Ada-D-Arg-Arg-cyclo[—(CH2)n—NH—CO—(CH2)k—NH—CO—(CH2)m—CO—N—CH2—CO-Hyp-Gly-Phe-N-]—CH2—CO-D-Phe-Phe-Arg-OH and pre-cyclic analogs.

Cyclic:

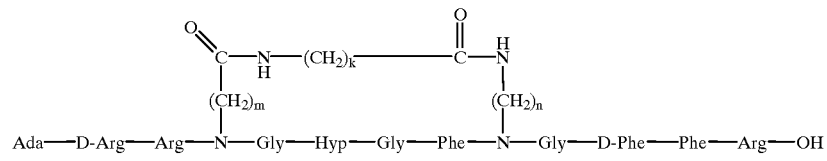

Ada—D-Arg—Arg—N—Gly—Hyp—Gly—Phe—N—Gly—D-Phe—Phe—Arg—OH precyclic:

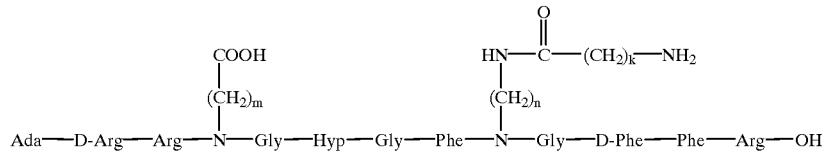

Ada—D-Arg—Arg—N—Gly—Hyp—Gly—Phe—N—Gly—D-Phe—Phe—Arg—OH k = 0; 2; 5
m = 2; 3
n = 2; 3; 4; 6

| CYCLIC PEPTIDES | | | | | PRECYCLIC PEPTIDES | | | |
|---|---|---|---|---|---|---|---|---|
| Peptide number | k | m | n | ring size | Peptide number | k | m | n |
| 305 | 0 | 2 | 2 | 19 | 318 | 0 | 2 | 2 |
| 306 | 0 | 2 | 3 | 20 | 319 | 0 | 2 | 3 |
| 307 | 0 | 3 | 3 | 21 | 320 | 0 | 3 | 3 |
| 308 | 0 | 3 | 4 | 22 | 321 | 0 | 3 | 4 |
| 309 | 0 | 2 | 6 | 23 | 322 | 0 | 2 | 6 |
| 310 | 0 | 3 | 6 | 24 | 323 | 0 | 3 | 6 |
| 311 | 2 | 3 | 3 | 25 | 324 | 2 | 3 | 3 |
| 312 | 2 | 3 | 4 | 26 | 325 | 2 | 3 | 4 |
| 313 | 2 | 2 | 6 | 27 | 326 | 2 | 2 | 6 |
| 314 | 2 | 3 | 6 | 28 | 327 | 2 | 3 | 6 |
| 315 | 5 | 3 | 4 | 29 | 328 | 5 | 3 | 4 |
| 316 | 5 | 2 | 6 | 30 | 329 | 5 | 2 | 6 |
| 317 | 5 | 3 | 6 | 31 | 330 | 5 | 3 | 6 |

No biological activity of this mixture has been found.

2% inhibition (mixture) at $10^{-5}$ M.

Example 5

H-D-Arg-Arg-cyclo[—(CH2)n—NH—CO—(CH2)k—NH—CO—(CH2)m—CO—N—CH2—CO-Hyp-Gly-Phe-N-]—CH2—CO-D-Phe-Phe-Arg-OH and pre-cyclic analogs.

Formula:
cyclic:

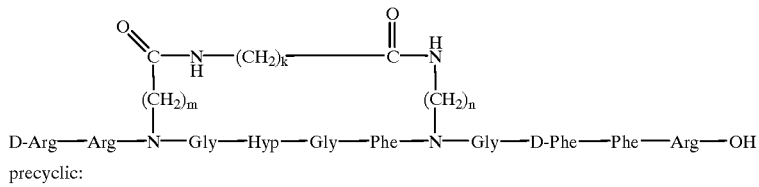

precyclic:

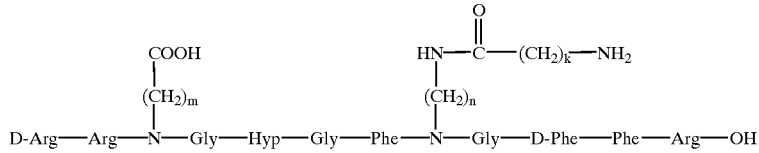

k = 0; 2; 5
m = 2; 3
n = 2; 3; 4; 6

29% inhibition (mixture) at $10^{-5}$ M.

Example 6

H-D-Arg-Arg-cyclo-[(CH2)n—CO—NH—(CH2)m—N—CH2—CO-Hyp-Gly-Phe-Xaa-]-D-Phe-Phe-Arg-OH and pre-cyclic analogs.

Formula:
cyclic:

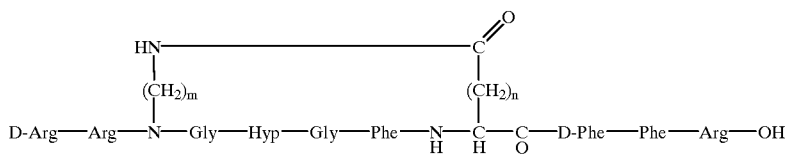

precyclic:

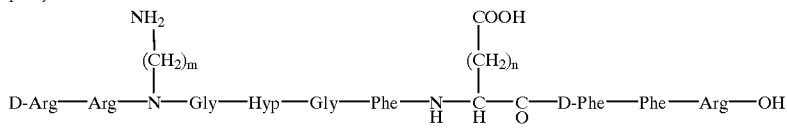

m = 2; 3; 4; 6
n = 1; 2
Xaa = D-Asp, Glu

CYCLIC PEPTIDES

| Peptide number | Xaa | m | n | ring size |
|---|---|---|---|---|
| 331 | D-Asp | 2 | 1 | 19 |
| 332 | D-Asp | 6 | 1 | 23 |
| 333 | Glu | 3 | 2 | 21 |
| 334 | Glu | 4 | 2 | 22 |
| 335 | Glu | 2 | 2 | 20 |
| 336 | Glu | 6 | 2 | 24 |

19% inhibition (mixture) at $10^{-5}$ M.
86% inhibition (peptides 331–332) at $5 \times 10^{-5}$ M.
16% inhibition (peptides 333–336) at $5 \times 10^{-5}$ M.
Peptide 331 was found to be inactive.
$K_d$ (peptide 332) = $2 \times 10^{-5}$ M.

PRECYCLIC PEPTIDES

| Peptide number | Xaa | m | n |
|---|---|---|---|
| 337 | D-Asp | 2 | 1 |
| 338 | D-Asp | 6 | 1 |
| 339 | Glu | 3 | 2 |
| 340 | Glu | 4 | 2 |
| 341 | Glu | 2 | 2 |
| 342 | Glu | 6 | |

No biological activity of this mixture has been found.

Example 7

Ada-D-Arg-Arg-cyclo-[(CH2)n—CO—NH—(CH2)m—N—CH2—CO-Hyp-Gly-Phe-Xaa-]-D-Phe-Phe-Arg-OH and pre-cyclic analogs.

Formula:
cyclic:

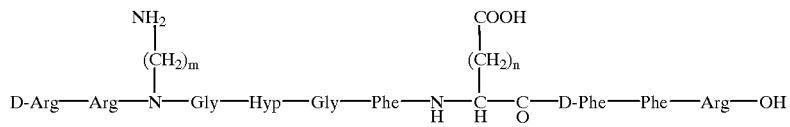

pre-cyclic:

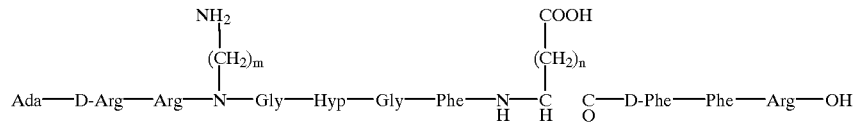

m = 2; 3; 4; 6
n = 1; 2
Xaa = D-Asp, Glu

PRECYCLIC PEPTIDES

| Peptide number | Xaa | m | n |
|---|---|---|---|
| 349 | D-Asp | 2 | 1 |
| 350 | Glu | 2 | 2 |
| 351 | Glu | 3 | 2 |
| 352 | Glu | 4 | 2 |
| 353 | D-Asp | 6 | 1 |
| 354 | Glu | 6 | 2 |

16% inhibition (mixture) at $10^{-5}$ M.

Example 8

D-Arg-Arg-cyclo-[(CH2)n—CO—NH—(CH2)m—N—CH2—CO-Hyp-Gly-Phe-Xaa-]-D-Phe-Phe-Arg-OH

CYCLIC PEPTIDES

| Peptide number | Xaa | m | n | ring size |
|---|---|---|---|---|
| 343 | D-Asp | 2 | 1 | 19 |
| 344 | D-Asp | 6 | 1 | 23 |
| 345 | Glu | 3 | 2 | 21 |
| 346 | Glu | 4 | 2 | 22 |
| 347 | Glu | 2 | 2 | 20 |
| 348 | Glu | 6 | 2 | 24 |

$K_d$ (mixture) = $8 \times 10^{-7}$ M.
78% inhibition (peptides 343 + 344) at $10^{-5}$ M.
54% inhibition (peptides 345 + 348) at $5 \times 10^{-5}$ M.

formula:

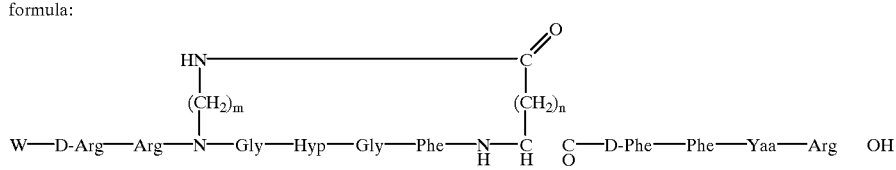

W=H, Adac (Adamantanecarboxylic acid)

m=2;3;4;6  n=1;2  Xaa=D-Asp, D-Glu  Yaa=Phe, Oic (Octahydroindole-3-carboxylic acid)

Synthesis: Peptides were prepared in SMPS bags, each one containing 60 mg Hydroxybenzyl resin (0.39 meq/gr). Because of the biological activity of the mixture, several new mixtures and then separate peptides were cleaved separately from the resin for biological screening.

CYCLIC PEPTIDES

| Peptide number | W | Xaa | Yaa | m | n | ring size |
|---|---|---|---|---|---|---|
| 368 | H | D-Asp | Oic | 2 | 1 | 19 |
| 369 | H | D-Glu | Phe | 2 | 2 | 20 |
| 370 | H | D-Glu | Phe | 3 | 2 | 21 |
| 373 | H | D-Asp | Phe | 3 | 1 | 20 |
| 374 | H | D-Asp | Phe | 4 | 1 | 21 |
| 371 | H | D-Glu | Phe | 4 | 2 | 22 |
| 372 | H | D-Glu | Phe | 6 | 2 | 24 |
| 375 | H | D-Asp | Oic | 6 | 1 | 23 |
| 376 | Adac | D-Asp | Phe | 2 | 1 | 19 |
| 377 | Adac | D-Asp | Oic | 2 | 1 | 19 |
| 378 | Adac | D-Asp | Phe | 6 | 1 | 23 |
| 379 | Adac | D-Asp | Oic | 6 | 1 | 23 |

Biological results:

peptides 373+374—20% inhibition at $10^{-7}$ M.

peptide 373—15% inhibition at $10^{-5}$ M.

peptide 374—18% inhibition at $10^{-7}$ M.

peptide 376—28% inhibition at $10^{-5}$ M.

peptide 378—$K_d=8\times10^{-7}$ M.

peptide 368—no activity was found.

peptide 375—18% inhibition at $10^{-7}$ M.

SUBSTANCE $P_{6-11}$ ANALOGS:

Example 9

Ac-Arg-Phe-Phe-cyclo-[(CH2)n—CO—NH—(CH2)m—N—CH2—CO-Leu-Xaa-]—NH2 and Ac-Arg-Phe-Phe-cyclo-[(CH2)n—CO—NH—(CH2)m—N—CH2—CO-Leu-N-]—CH2—CO—NH2 and their pre-cyclic analogs.

Synthesis: Peptides were prepared in SMPS bags, each one containing 100 mg MBHA resin (0.57 meq/gr) and screened for biological activity on GPI. Peptides from the most active cyclic and pre-cyclic mixtures (5C and 5L respectively) were cleaved separately from the resin, purified by preparative HPLC, characterized by TOF-MS and AAA and detected for their biological activity on GPI.

MIXTURES

| Mixture number | Structure | Number of peptides | EC$_{50}$ (nM) Without atropine | EC$_{50}$ (nM) With atropine[1] |
|---|---|---|---|---|
| 1C | Xaa = L-Asp, L-Glu | 8 | 5000 | n.d. |
| 2C | Xaa = D-Asp, D-Glu | 8 | >10,000 | n.d. |
| 3C | Xaa = Gly units Rings size = 13, 14 | 3 | >10,000 | n.d. |
| 4C | Xaa = Gly units Ring size = 15, 16 | 4 | >10,000 | n.d. |
| 5C | Xaa = Gly units Ring size = 17, 18, 20 | 5 | 3000 | 4000 |
| 1L | Xaa = L-Asp, L-Glu | 8 | 600 | 1000 |
| 2L | Xaa = D-Asp, D-Glu | 8 | 4000 | 3000 |
| 3L | Xaa = Gly units Ring size = 13, 14 | 3 | 1600 | 1000 |
| 4L | Xaa = Gly units Ring size = 15, 16 | 4 | >10,000 | n.d. |
| 5L | Xaa = Gly units Ring size = 17, 18, 20 | 5 | 600 | 750 |

[1]n.d. = not detected when the value without atropine was equal to or bigger than 5000 nM.

Formula:
cyclic:

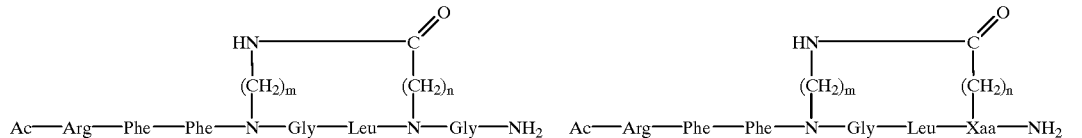

pre-cyclic:

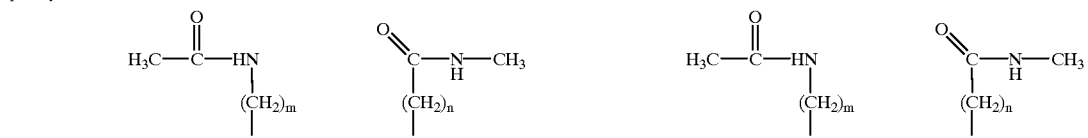

m = 2, 3, 4, 6
n = 1, 2, 3, 4, 5
Xaa = L-Asp, D-Asp, D-Glu

Example 10

Bicyclic SP$_{6-11}$ analogs.

Formula:

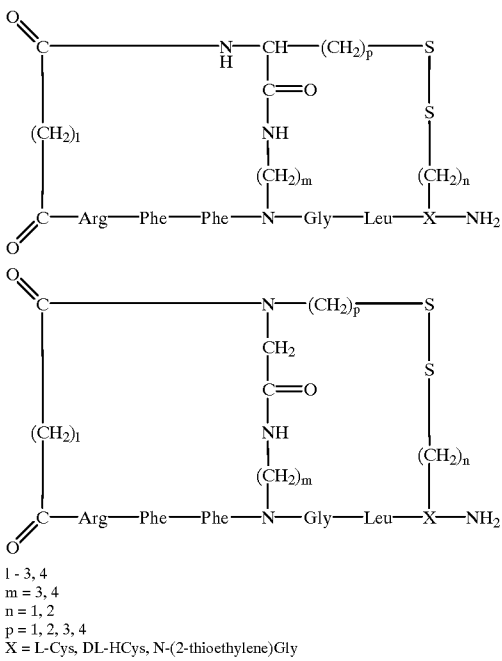

l - 3, 4
m = 3, 4
n = 1, 2
p = 1, 2, 3, 4
X = L-Cys, DL-HCys, N-(2-thioethylene)Gly Synthesis: Peptides were prepared in SMPS bags, each one containing 100 mg MBHA resin (0.57 meq/gr). The (-amino group of the building unit in position 9 was protected by Boc. After coupling of this building unit to Leu10 the Boc group was removed and to the w-amine was coupled a second S-benzyl protected w-thiol building unit or amino acid with its a-amine protected with Boc. Then the Fmoc group was removed from the a-amine of the building unit in position 9 and the synthesis of the peptides was continued. After completion of the synthesis of the hexapeptide chain, a dicarboxylic acid was coupled to the amino terminus and then the Boc group protecting the a-amino group of the w-thiol containing building unit or amino acid was removed and the lactam ring was closed with 6 eq of TBTU and repetition of cyclization 3 times. Then the disulfide ring was closed by the above mentioned solid-phase diphenylsulfoxide-silyl chloride method. Peptides mixtures were cleaved from the resin using HF/thioanisole at 0–5° C. and screened for biological activity on GPI. Since the yields of these peptides were relatively low due to side-reactions in the disulfide formation step, the peptides comprising the most active mixture (M4) were re-synthesized on 500 mg of resin and cyclized separately after cleavage from the resin by the normal solution diphenylsulfoxide-silyl chloride method.

BPI LIBRARIES:
Introduction:

BPI$_{23}$ is an amino terminal recombinant fragment of the natural 55-KDa cationic protein bactericidal/permeability increasing protein (BPI, Little et. al. 1994, J. Biol. Chem. 269:1865–1872). The BPI$_{23}$ fragment has all the antibacterial and antiendotoxin properties of the holoprotein against Gram-negative bacteria. Epitope mapping of the active fragment yielded a 15 amino acids bactericidal peptide. Later, another domain was found to have anti-fungal activity. The 10-mer linear peptide: Lys-Trp-Leu-Ile-Gln-Leu-Phe-His-Lys-Lys-NH (amino acids 152–161 in the BPI$_{23}$ sequence), served as our basic sequence for producing backbone-cyclic peptide libraries in the aim of developing anti-fungal peptidomimetic drugs with higher potency, less toxicity and longer half-life than linear peptides.

Usually, for identifying the amino acids critical for activity and those that might be replaced (by building units in our case), one would perform an "Alanine scan" substituting each amino acid in the sequence by Alanine and testing the influence on the peptide activity. Because of the fact that no information was available on the conformation and the structure-activity-relationship of the basic active linear deca-peptide we decided to define the optimal cyclization points within the linear sequence directly by synthesis of backbone-cyclic peptide libraries.

The first BPI library that was synthesized (IG-BPI1), contained various cyclization points between positions 153–160 (because of synthetic and rational reasons, the Lys residues of positions 152 and 160 were not substituted). The goal was to determine whether a particular bridge position is favored and which amino acids in the linear sequence can not be substitute. The backbone-cyclic, the pre-cyclic and the linear (actually a double "Glycine scan"), libraries were synthesized and tested. The anti-fungal results, indicate that the activity was preserved to a significant extend in the cyclic peptides. Overall, pre-cyclic peptides were less active than either the corresponding backbone cyclic peptides or linear peptides. Sub-library A6 in which the backbone cyclic peptides were more active than the linear, was the most interesting sub-library, although the differences between the four backbone cyclic sub-libraries were not large. The information obtained from the backbone-cyclic library with additional information from separate backbone-cyclic analogs, served as basis for the design of the next BPI backbone-cyclic libraries.

Biological Evaluations of BPI Libraries:

The BPI libraries were tested for their anti Candida albicans activity in an in-vitro radial diffusion assay. Briefly, candida are incorporated into agarose and a series of wells are punched into the solidified agarose. A small volume of each library/sub-library sample (serially diluted) is placed into each well and allowed to diffuse into the agarose. An overlayer is then poured over the plate and the assay is incubated overnight. Fungicidal zones are measured with a micrometer for each sample dilution. The amount of peptide added to the well that create a net 30 mm2 zone gives the recorded activity result. For a given sample to create a radial diffusion zone, the candida must be killed, therefore this assay distinguish between fungicidal and fungistatic compounds.

In order to validate positive signals of the anti-fungal tests, and to eliminate non-specific signals, library samples of somatostatin-peptides that were synthesized and handled in the same procedures and assume to contain the same contaminants, were tested in the same assays as negative control samples. These samples had no activity in any of the anti-fungal assays.

In addition, the sub-library samples are tested in the radial diffusion assay after incubation in human serum for testing the metabolic stability of these samples and comparison between the stability of backbone-cyclic vs. pre-cyclic and linear libraries.

Solid-phase-release Assay for Anti-fungal and Anti-bacterial Activity Evaluation of BPI and Other Peptide Libraries:

1. Peptides are anchored to the beads by a linker that: is cleavable by natural pH treatment (Salmon et. al. Proc. Natl. Acad. Sci. 90, 11708–11712, 1993), the beads are placed in agarose as for radial diffusion assay and the peptides are cleaved to the surrounded media and will inhibit the fungi growth.

2. The peptides are synthesized on non-cleavable linker, the beads are placed as above into the agarose and the peptides will inhibit the growth of the fungi or bacteria by binding to essential factors (enzymes etc.) in the media, or cell membrane components.

Table I summarize some of the libraries of BPI that were synthesized and characterized. Position numbers of amino acids in the BPI peptides are based on the sequence of the native $BPI_{23}$ protein.

Example 11

IG-BPI1 LIBRARY

This library was synthesized with the aim of finding the best position of the bridge in the basic linear deca-peptide. In each of positions 153–160 either a native amino acid or a building unit (Gly-C2 in positions 153, 154, 155 or 156 and Gly-N2 in positions 157, 158, 159 or 160) was coupled, yielding four sub-libraries including four peptides in each. The sub-libraries differ between them in the position of thus Gly-C2 unit, while peptides in each sub-library differ in the position of the Gly-N2 unit. The linear library contain non-modified Gly instead of the building units thus, serve as indication for the necessity of the linear peptide's side-chain groups for activity. The synthesis is illustrated in the following scheme.

TABLE I

The composition of several BPI libraries.

| Library Name | Library Type | Sequence per position | | | | | | | | | |
|---|---|---|---|---|---|---|---|---|---|---|---|
| | | 152 | 153 | 154 | 155 | 156 | 157 | 158 | 159 | 160 | 161 |
| IG-BPI1 | backbone-cyclic | Lys | Trp | Leu | Ile | Gln | Leu | Phe | His | Lys | Lys |
| | | | Gly-C2 | Gly-C2 | Gly-C2 | Gly-C2 | Gly-N2 | Gly-N2 | Gly-N2 | Gly-N2 | |
| | pre-cyclic | Lys | Trp | Leu | Ile | Gln | Leu | Phe | His | Lys | Lys |
| | | | Gly-C2 | Gly-C2 | Gly-C2 | Gly-C2 | Gly-N2 | Gly-N2 | Gly-N2 | Gly-N2 | |
| | linear | Lys | Trp | Leu | Ile | Gln | Leu | Phe | His | Lys | Lys |
| | | | Gly | Gly | Gly | Gly | Gly | Gly | Gly | Gly | |
| IG-BPI3 | backbone-cyclic | Lys | Trp | Leu | Ile | Gly-C2 | Leu | Phe | His | Gly-N2 | Lys |
| | | | | | Gly | | | DPhe | | | |
| | | | | | Ala | | | Phg | | | |
| | | | | | none | | | pNO2Phe | | | |
| | | | | | | | | pFPhe | | | |
| | pre-cyclic | Lys | Trp | Leu | Ile | Gly-C2 | Leu | Phe | His | Gly-N2 | Lys |
| | | | | | Gly | | | DPhe | | | |
| | | | | | Ala | | | Phg | | | |
| | | | | | Des | | | pNO2Phe | | | |
| | | | | | | | | pFPhe | | | |
| IG-BPI4 | backbone-cyclic | Lys | 2Nal | Gly-C1 | Ile | Gln | Leu | Phe | Gly-N2 | Lys | Lys |
| | | | D2Nal | Gly-C2 | | | | | Gly-N3 | | |
| | | | 1Nal | Gly-N2 | | | | | Gly-C1 | | |
| | | | D1Nal | Gly-N3 | | | | | Gly-C2 | | |
| | pre-cyclic | Lys | 2Nal | Gly-C1 | Ile | Gln | Leu | Phe | Gly-N2 | Lys | Lys |
| | | | D2Nal | Gly-C2 | | | | | Gly-N3 | | |
| | | | 1Nal | Gly-N2 | | | | | Gly-C1 | | |
| | | | D1Nal | Gly-N3 | | | | | Gly-C2 | | |

All peptides have an amide C-terminal

IG-BPI1-LIBRARY

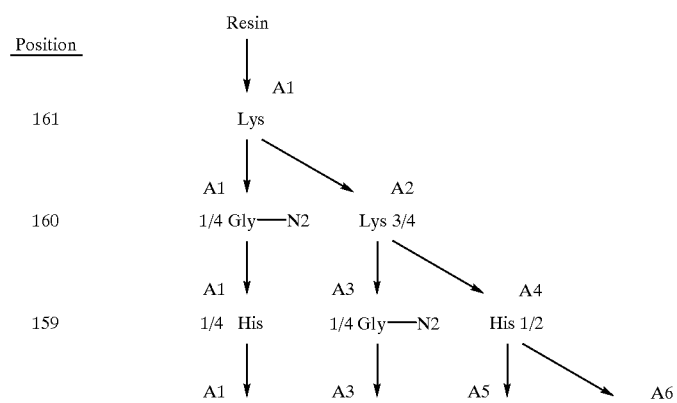

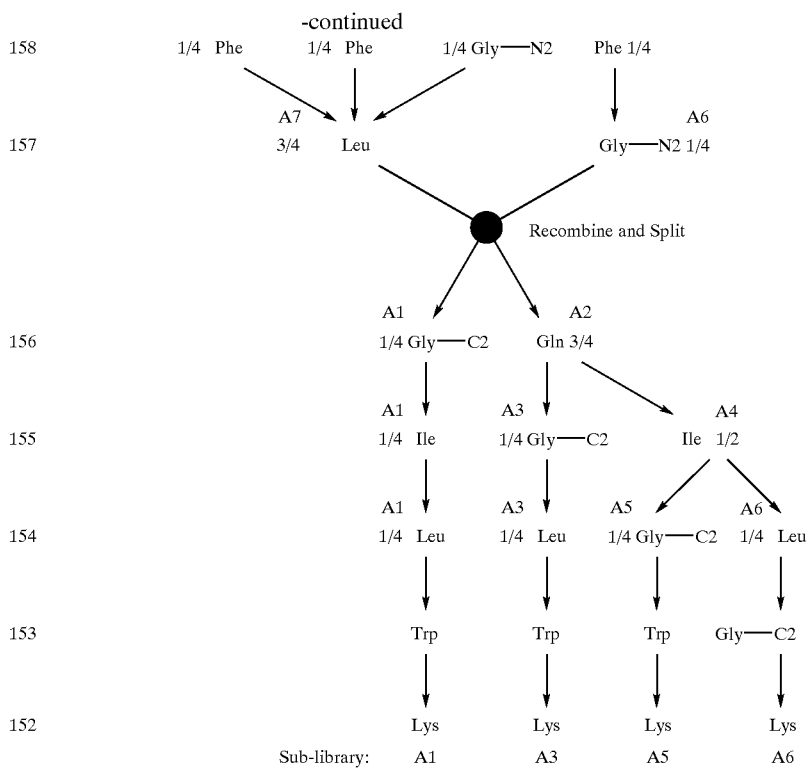

As can be seen from the anti-fungal activity results, the backbone-cyclic peptides have improved activity over the pre-cyclic peptides. In one case, sub-library A6, the activity of the backbone-cyclic peptides is even better than the linear sequence.

Example 12

IG-BPI3 LIBRARY

The synthesis scheme of this library containing total of 20 peptides in 4 sub-libraries is described in the following scheme. One of the sub-libraries (A) contains nona-peptides instead of deca-peptides. This was done in order to test the importance of the Ile residue at position 155 (amino acid indicated as "Des" in the composition table), for activity and to check wherever it is possible to substitute or preferably, delete it from the original sequence. The backbone-cyclic and the pre-cyclic libraries were synthesized simultaneously.

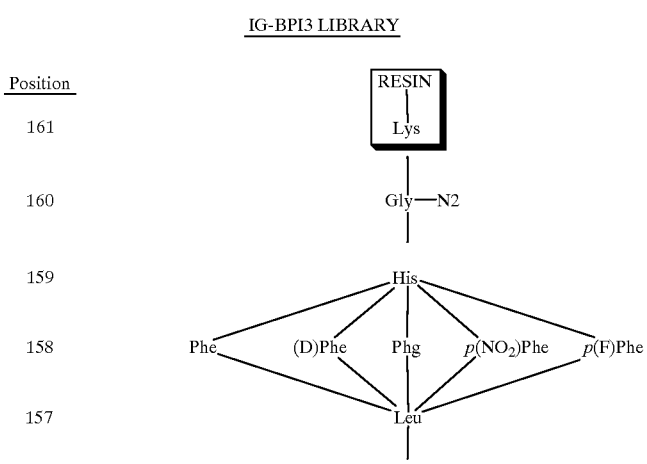

IG-BPI3 LIBRARY

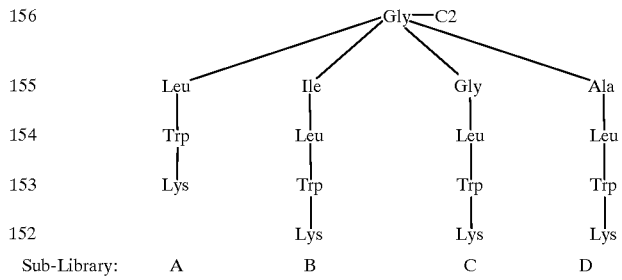

| | | | | Gly—C2 | | | | |
|---|---|---|---|---|---|---|---|---|
| 156 | | | | | | | | |
| 155 | Leu | Ile | Gly | Ala | | | | |
| 154 | Trp | Leu | Leu | Leu | | | | |
| 153 | Lys | Trp | Trp | Trp | | | | |
| 152 | | Lys | Lys | Lys | | | | |
| Sub-Library: | A | B | C | D | | | | |

The sub-libraries were tested for their anti-fungal activity in the radial diffusion assay and the results are summarized in table II.

TABLE II

Composition and anti-fungal activity of IG-BPI1 library.

| Sub-library | Peptide sequence Position | | | | | | | | | | Amount needed for anti-fungal activity[1] Backbone | | |
|---|---|---|---|---|---|---|---|---|---|---|---|---|---|
| | 152 | 153 | 154 | 155 | 156 | 157 | 158 | 159 | 160 | 161 | cyclic | Pre-cyclic | Linear |
| A1 | Lys | Trp | Leu | Ile | Gly-C2 | Leu | Phe | His | Gly-N2 | Lys | 12.2 | 27.0 | 2.1 |
| | Lys | Trp | Leu | Ile | Gly-C2 | Leu | Phe | Gly-N2 | Lys | Lys | | | |
| | Lys | Trp | Leu | Ile | Gly-C2 | Leu | Gly-N2 | His | Lys | Lys | | | |
| | Lys | Trp | Leu | Ile | Gly-C2 | Gly-N2 | Phe | His | Lys | Lys | | | |
| A3 | Lys | Trp | Leu | Gly-C2 | Gln | Leu | Phe | His | Gly-N2 | Lys | 17.4 | 36.2 | 7.47 |
| | Lys | Trp | Leu | Gly-C2 | Gln | Leu | Phe | Gly-N2 | Lys | Lys | | | |
| | Lys | Trp | Leu | Gly-C2 | Gln | Ley | Gly-N2 | His | Lys | Lys | | | |
| | Lys | Trp | Leu | Gly-C2 | Gln | Gly-N2 | Phe | His | Lys | Lys | | | |
| A5 | Lys | Trp | Gly-C2 | Ile | Gln | Leu | Phe | His | Gly-N2 | Lys | 30.4 | 44.6 | 18.1 |
| | Lys | Trp | Gly-C2 | Ile | Gln | Leu | Phe | Gly-N2 | Lys | Lys | | | |
| | Lys | Trp | Gly-C2 | Ile | Gln | Leu | Gly-N2 | His | Lys | Lys | | | |
| | Lys | Trp | Gly-C2 | Ile | Gln | Gly-N2 | Phe | His | Lys | Lys | | | |
| A6 | Lys | Gly-C2 | Leu | Ile | Gln | Leu | Phe | His | Gly-N2 | Lys | 8.9 | 65.5 | 17.5 |
| | Lys | Gly-C2 | Leu | Ile | Gln | Leu | Phe | Gly-N2 | Lys | Lys | | | |
| | Lys | Gly-C2 | Leu | Ile | Gln | Leu | GIy-N2 | His | Lys | Lys | | | |
| | Lys | Gly-C2 | Leu | Ile | Gln | Leu | Phe | His | Lys | Lys | | | |

[1]The amount of peptide sample (in μg) added to the well to create a net 30 mm² fungal-inhibition zone.

Example 13

IG-BPI4 LIBRARY

The composition of this library, as illustrated in the following scheme was based on an active peptide (synthesized and tested separately) with the sequence: Lys-D1Nal-[Gly-C2-Ile-Gln-Leu-Phe-Gly-N2]-Lys-Lys-NH2. With the aim of finding the best bridge size and orientation, four different building units (Gly-C1, Gly-C2, Gly-N2 and Gly-N3), were used for cyclization between positions 154 and 159. Simultaneously, the influence of different Naphtylalanine (Nal) residues at position 153 was also evaluated. The 4 sub-libraries differ in their residue at position 153 and the peptides (total 32) in each sub-libraries differ in their bridge type or size. For rapid identification of the preferred bridging building unit at position 154, portions from each of the four peptide-resins (with positions 161–154), after coupling of the building units, were removed before recombination and kept. After identification of the active sub-library (by the anti-fungal assay), the "best" Naphtylalanine residue will be coupled to each of the 4 resin portions. After coupling of Lys to each (position 152) portion, the new 4 sub-libraries will be tested for their activity.

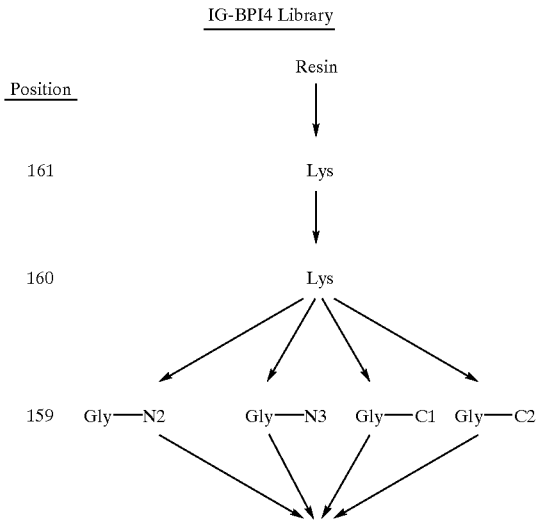

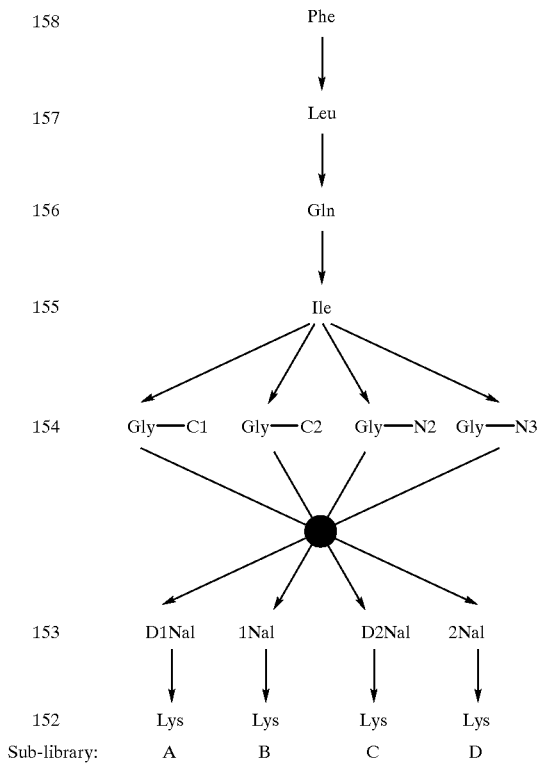

SOMATOSTATIN ANALOGS:
Biological Screening of Somatostatin Libraries:

The peptide libraries and sub-libraries were tested for their potency in inhibition of the binding of 125I-Tyr11-SRIF (based on the method described by Raynor et. al. 1993 Molecular Pharmacology 43, 838–844) to membrane preparations expressing the somatostatin receptors (SSTR-1,2,3,4 or 5). The receptor preparations used for these tests were either from the cloned receptors selectively expressed in Chinese Hamster Ovary (CHO) cells or from cell lines naturally expressing the SSTRs. In order to validate positive signals of the binding tests, and to eliminate non-specific signals, library samples of BPI-peptides that were synthesized and handled in the same procedures and assume to contain the same contaminants, were tested in the same assays as negative control samples. These samples had no binding activity in any of the assays.

The libraries are further tested in-vitro for their influence on cyclic adenosine monophosphate (cAMP) levels, tyrosine phosphatase activity, growth hormone secretion, and cell growth.

The libraries are further tested in-vivo, for the inhibition of growth-hormone release, amylase, gastric acid, insulin and glucagon secretion in animals.

Solid-phase Somatostatin Assays:

Production and screening of peptide libraries attached to a solid-phase support have many advantages and may enhance the effort of finding the active molecule.

One type of bead-binding-assay was developed with a known active somatostatin analog anchored to beads. The peptide BIM-23052 (a known somatostatin analog with the sequence: NH2-DPhe-Phe-Phe-DTrp-Lys-Thr-Phe-Thr-NH) was synthesized on TentaGel-NH2 beads (these beads does not allow cleavage of the peptides), by peptide synthesizer (Applied biosystems 433A), using the recommended procedure. The side-chain protecting groups were removed by treatment with TFA and scavengers and the beads were washed and dried. Few approaches are tested:

1. Peptides that binds the somatostatin receptors can bind also to antibodies against SRIF-14 (the native SST peptide) this was shown in a work utilized monoclonal antibodies for successful screening of phage peptide libraries (Bio/Technology 13;165–169, 1995) and selection of active analogs. Monoclonal and polyclonal antibodies against SRIF-14 were incubated with beads carrying the BIM-23052 peptide (after blocking non-specific sites with 1% BSA in PBS containing 0.05% Tween 20 and 0.05% NaN3). After washes with PBS-T (PBS containing 0.05% Tween-20), each of the resin portions (reacted with either the poly- or the monoclonal antibodies), were divided into two parts and incubated with alkaline-phosphatase conjugate to anti-rabbit or anti-mouse IgG (diluted in blocking buffer). Each incubation was for 30–45 minutes at RT. After additional washes, a substrate solution (BCIP or BCIP/NBT) was added to each of the portions. The results indicated specific staining (blue or purple color) of the beads reacted with the appropriate antibodies (polyclonal followed by anti-rabbit antibodies and monoclonal followed by anti-mouse antibodies), and no staining when the non fitting antibody combination (polyclonal followed by anti-mouse antibodies or monoclonal followed by anti-rabbit antibodies), was added. In a similar approach anti-idiotypic antibodies against the somatostatin receptor/s are used for direct screening of the positive and negative beads and for bead-supported libraries.

2. Affinity selection. Selective somatostatin receptors membrane preparations are incubated with bead-supported peptides (after blocking as above), after washes, the membrane-receptors are eluted from the beads and the eluted material are quantify by reacting with 125I-SRIF as done in the above binding assay.

3. Soluble samples of peptide libraries are tested for there ability to inhibit the binding of biotinylated-SRIF to polyclonal antibodies against SRIF, absorbed to microtiter plate wells. Briefly, microtiter plate wells are coated with 5 ug/ml solution of antibodies, after 16 hours incubation at RT., the wells are blocked (blocking and wash solutions as in method 1) for 1 hour at RT. N-terminal biotinylated-SRIF is added to the wells at a concentration of 10–6 M together with library samples in different concentrations, in blocking buffer. After 1–2 hours incubation at RT, the wells are washed several times and an Avidin-alkaline phosphatase solution is added to the wells for 30 minutes incubation. After additional washes, the signal is developed using the PNPP substrate yielding a soluble product that its optical density can be recorded at 405 nm. The assay may be performed with any somatostatin analog that can be biotinylated without loss of binding activity and that antibodies that inhibit its binding to the receptors are available.

4. Soluble samples of peptide libraries are tested for their ability to inhibit the binding of antibodies against SRIF to peptides linked to solid-phase support (micro wells, beads, MultiPin crowns, cellulose filter etc.). The SRIF peptides are directly synthesized on the solid-phase support or chemically linked to the solid support after synthesis. After blocking (solutions as in method 1), the segmented support is incubated with an antibody solution together with library samples in different concentrations in blocking buffer. After washes, a second antibody-alkaline phosphatase solution is added and after incubation and washes the signal is developed using the PNPP substrate yielding a soluble product that its optical density can be recorded at 405 nm. The assay may be performed with any somatostatin analog that can be biotinylated without loss of binding activity and that antibodies that inhibit its binding to the receptors are available.

Table III summarizes some of the libraries of somatostatin that were synthesized and characterized. The composition of the libraries was based on a few known somatostatin analogs. Position numbers of amino acids in the somatostatin sequence are based on the native somatostatin peptide (SRIF-14, Raynor et. al. ibid).

TABLE III

The composition of several Somatostatin libraries.

| Library Name | Library Type | Sequence per position | | | | | | | |
|---|---|---|---|---|---|---|---|---|---|
| | | 5 | 6 | 7 | 8 | 9 | 10 | 11 | 12 |
| VH-SST1 | backbone-cyclic | DPhe Pro Val Leu Gly | Gly-C2 | Phe | DTrp Leu | Lys Pro | Gly Val | Gly-N2 | Val |
| | pre-cyclic | DPhe Pro Val Leu Gly | Gly-C2 | Phe | DTrp Leu | Lys Pro | Gly Val | Gly-N2 | Val |
| | linear | DPhe Pro Val Leu Gly | Gly | Phe | DTrp Leu | Lys Pro | Gly Val | Gly-N2 | Val |
| IG-SST1 | backbone-cyclic | DPhe Phe DTrp Trp | Gly-C2 | Phe | DTrp Phe Leu | Lys | Gly-N2 | Phe Ala Leu | Val |
| | pre-cyclic | DPhe Phe DTrp Trp | Gly-C2 | Phe | DTrp Phe Leu | Lys | Gly-N2 | Phe Ala Leu | Val |
| | linear | DPhe Phe DTrp Trp | Gly | Phe | DTrp Phe Leu | Lys | Gly | Phe Ala Leu | Val |
| YS-SST1 | backbone-cyclic | DPhe | Gly-C1 Gly-C2 Gly-N2 Gly-N3 | Phe | DTrp | Lys | Thr | Gly-N2 Gly-N3 Gly-C1 Gly-C2 | Thr |
| | pre-cyclic | DPhe | Gly-C1 Gly-C2 Gly-N2 Gly-N3 | Phe | DTrp | Lys | Thr | Gly-N2 Gly-N3 Gly-C1 Gly-C2 | Thr |
| YS-SST2 | backbone-cyclic | DPhe | Gly-N3 | Phe Tyr pClPhe pNO2Phe | DTrp | Lys | Thr Ser Val Abu | Gly-C2 | Thr 2Nal D2Nal |
| | pre-cyclic | DPhe | Gly-N3 | Phe Tyr pClPhe pNO2Phe | DTrp | Lys | Thr Ser Val Abu | Gly-C2 | Thr 2Nal D2Nal |
| YS-SST3 | backbone-cyclic | DPhe Gly | Phe-N2 Phe-N3 | Phe | DTrp | Lys | Thr Ser Gly | Phe-C2 | Thr |
| | pre-cyclic | DPhe Gly | Phe-N2 Phe-N3 | Phe | DTrp | Lys | Thr Ser Gly | Phe-C2 | Thr |
| YS-SST4A | backbone-cyclic | | Phe-C2 | DVal DAla DLeu | DLys DOrn | Trp Thi | DTyr | Gly-N2 Gly-N3 | Phe |
| YS-SST4B | backbone-cyclic | Thr | Phe-C2 | DVal DAla DLeu | DLys DOrn | Trp Thi | DTyr | Gly-N2 Gly-N3 | Phe |
| YS-SST5 | backbone-cyclic | D2Nal 2Nal D1Nal 1Nal | Gly-C1 Gly-C2 Gly-N2 Gly-N3 | Tyr | DTrp | Lys | Val DVal | Gly-N2 Gly-N3 Gly-C1 Gly-C2 | Thr |
| | pre-cyclic | D2Nal 2Nal D1Nal 1Nal | Gly-C1 Gly-C2 Gly-N2 Gly-N3 | Tyr | DTrp | Lys | Val DVal | Gly-N2 Gly-N3 Gly-C1 Gly-C2 | Thr |
| VHSST-6 | backbone-cyclic | | Phe-C1 Phe-C2 | Phe pNO2Phe Phg | DTrp DThi | Lys Orn | Gly-N2 | Phe | |

All peptides have an amide C-terminal

Example 14
VH-SST1 LIBRARY

The library was designed to contain 40 backbone cyclic peptides in final 5 sub-libraries, each containing 8 different peptides. Total synthesis scale was 0.2 mmol. Before the last coupling step, the resin was split into 5 portions, coupling was performed for each with different AA. and left as separate sub-libraries for all other steps (Fmoc, Dde and Allyl/Alloc deprotection, cyclization and cleavage). For this library, the Lys (-amine was protected with Dde that was removed before cleavage by double treatment with 2% hydrazine hydrate in NMP for a total period of 30 minutes. Mixture C (as described under general synthesis), was used for cleavage.

The backbone-cyclic library was synthesized and then the pre-cyclic and the linear libraries.

Before cleavage, about 10% of each sub-library resin was removed, washed, dried and kept as bead-attached sub-libraries for testing in a solid-phase-assays. The binding of polyclonal antibodies against SRIF-14 was tested with these sub-libraries (example 16).

The sub-library samples were tested for inhibition of 125I-Tyr11-SRIF to membrane preparations expressing the rat somatostatin receptor 5. The results are summarized in Table IV.

TABLE IV

Inhibition of $^{125}$I-Tyr$^{11}$-SRIF binding to selectively expressed rat somatostatin receptor 5.

| Sub-library | N-terminal amino acid | Inhibition of $^{125}$I-Tyr$^{11}$-SRIF binding (%) | | | | | |
|---|---|---|---|---|---|---|---|
| | | Backbone-cyclic | | | Pre-cyclic | | |
| | | $10^{-6}$M | $10^{-7}$M | $10^{-8}$M | $10^{-6}$M | $10^{-7}$M | $10^{-8}$M |
| A | DPhe | 54 | 14 | 4 | 64 | 26 | 9 |
| B | Pro | 62 | 30 | 8 | 70 | 37 | 11 |
| C | Val | 57 | 16 | 7 | ND | ND | ND |
| D | Leu | 78 | 44 | 12 | ND | ND | ND |
| E | Gly | 85 | 55 | 17 | ND | ND | ND |

Example 15
IG-SST1-LIBRARY

In this somatostatin library, the bridge was constant between position 6 with Gly-C2 and position 10 with Gly-N2. The library contain 36 peptides in 4 sub-libraries, the backbone-cyclic library and the pre-cyclic libraries are synthesized simultaneously. The linear library was synthesized separately. As in VH-SST2 library, bead-attached sub-libraries were removed before cleavage and tested for binding to polyclonal antibodies against SRIF.

Example 16
BEAD-BINDING ASSAY FOR VH-SST2 AND IG-SST1 LIBRARIES

Beads from each of the backbone-cyclic, the pre-cyclic and the linear sub-library samples were tested for binding of rabbit polyclonal against SRIF-14. The bead attached BIM-23052 peptide served as a positive control sample since it was found to be specifically recognized by poly- and monoclonal antibodies against SRIF-14. The sub-library peptide-beads were washed, blocked and incubated with the first (polyclonal anti SRIF-14), and second (goat anti rabbit coupled to alkaline phosphatase), antibodies. Color development was performed using the BCIP substrate yielding insoluble blue precipitation on positive beads. The resulted blue staining of the sub-libraries are summarized in Table V.

TABLE V

Staining of VH-SST1 and IG-SST1 libraries with antibodies against SRIF-14

| Sub-library | | Staining[1] | Sub-library | | Staining[1] |
|---|---|---|---|---|---|
| VH-SST1-A | Cyclic | 0 | IG-SST1-A | Cyclic | 1 |
| | Pre-cyclic | 4 | | Pre-cyclic | 2 |
| | Linear | 0 | | Linear | 0 |
| VH-SST1-B | Cyclic | 2 | IG-SST1-B | Cyclic | 3 |
| | Pre-cyclic | 4 | | Pre-cyclic | 2 |
| | Linear | 2 | | Linear | 0 |
| VH-SST1-C | Cyclic | 0 | IG-SST1-C | Cyclic | 1 |
| | Pre-cyclic | 2 | | Pre-cyclic | 5 |
| | Linear | 2 | | Linear | 0 |
| VH-SST1-D | Cyclic | 0 | IG-SST1-D | Cyclic | 3 |
| | Pre-cyclic | 2 | | Pre-cyclic | 4 |
| | Linear | 1 | | Linear | 0 |
| VH-SST1-E | Cyclic | 0 | | | |
| | Pre-cyclic | 3 | BIM-23052 | Linear | 2 |
| | Linear | 2 | | | |

[1]Staining score is given as an arbitrary number between 1–5, relative to the percentage of stained beads in each group and the average density of staining.

Example 17
YS-SST1 LIBRARY

This library was designed in order to optimize the bridge size and type between positions 6 and 10 or positions 6 and 11. The library include constant amino acids at positions 5,7,8,9,12, and different building units in position 6, 10 and 11. Each of the 4 sub-libraries contains 4 peptides differ in their bridge type as described in table VI.

TABLE VI

Sub-libraries of YS-SST1 library

| Sub-library | Position 11 | Position 10 | Position 6 | Bridge positions: |
|---|---|---|---|---|
| A 1-2 | Gly-N2 | Thr | Gly-C1 | 6–11 |
| | Gly-N3 | | Gly-C2 | |
| A 3-4 | Gly-C1 | Thr | Gly-N2 | 6–11 |
| | Gly-C2 | | Gly-N3 | |
| B 1-2 | Phe | Gly-N2 | Gly-C1 | 6–10 |
| | | Gly-N3 | Gly-C2 | |
| B 3-4 | Phe | Gly-C1 | Gly-N2 | 6–10 |
| | | Gly-C2 | Gly-N3 | |

The library synthesis is illustrated in the following scheme.

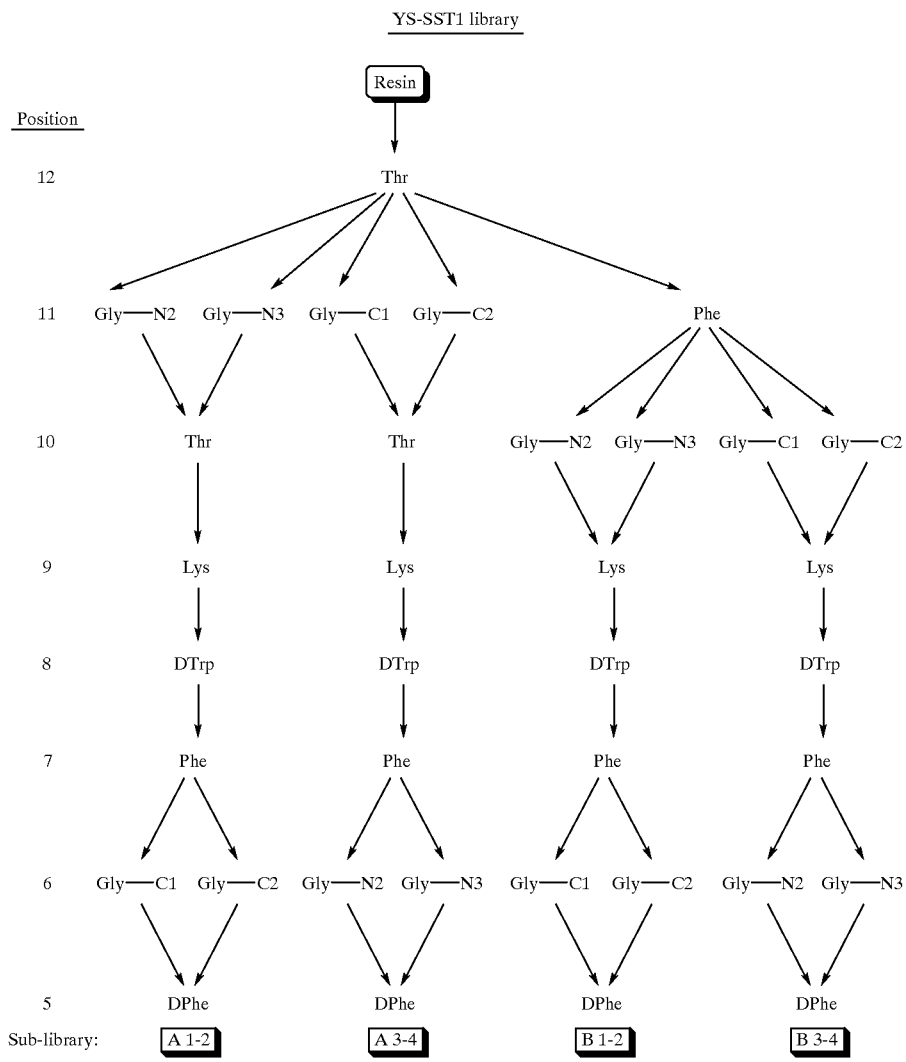

Synthesis yields of this library were: 3.5 mg (average) for backbone-cyclic peptides and 3.2 for pre-cyclic peptides. The linear "library" in this case contains only two analogs: DPhe-Gly-Phe-DTrp-Lys-Thr-Gly-Thr-NH2 and DPhe-Gly-Phe-DTrp-Lys-Gly-Phe-Thr-NH2, That were synthesized separately.

The sub-libraries were tested for inhibition of 125I-Tyr11-SRIF to membrane preparations expressing the rat somatostatin receptor 5. The results are summarized in table VII.

TABLE VII

Inhibition of $^{125}$I-Tyr$^{11}$-SRIF binding to selectively expressed rat somatostatin receptor −5.

| | Inhibition of $^{125}$I-Tyr$^{11}$-SRIF binding (%) | | | | | |
|---|---|---|---|---|---|---|
| | Backbone-cyclic | | | Pre-cyclic | | |
| Sub-library | $10^{-6}$M | $10^{-7}$M | $10^{-8}$M | $10^{-6}$M | $10^{-7}$M | $10^{-8}$M |
| A 1-2 | 64 | 18 | 0 | 38 | 5 | 0 |
| A 3-4 | ND | ND | ND | 55 | 14 | 7 |

TABLE VII-continued

Inhibition of $^{125}$I-Tyr$^{11}$-SRIF binding to selectively expressed rat somatostatin receptor −5.

| | Inhibition of $^{125}$I-Tyr$^{11}$-SRIF binding (%) | | | | | |
|---|---|---|---|---|---|---|
| | Backbone-cyclic | | | Pre-cyclic | | |
| Sub-library | $10^{-6}$M | $10^{-7}$M | $10^{-8}$M | $10^{-6}$M | $10^{-7}$M | $10^{-8}$M |
| B 1-2 | ND | ND | ND | 54 | 15 | 0 |
| B 3-4 | 38 | 5 | 0 | 68 | 24 | 6 |

ND — not determined

Example 18

YS-SST2 LIBRARY

This library was designed to contain a constant bridge between two building units at positions 6 and 11, constant amino acids at positions 5, 8, and 9, and diversity in positions 7, 10, and 12. The library contains 4 sub-libraries, differing between themselves in the amino acid at position 7.

Example 19

YS-SST3 LIBRARY

In this library Phe-building units were incorporated at positions 11 and 6 (Phe-N2 and Phe-N3 in position 6 and Phe-C2 in position 11). In the positions after these units, different amino acids were coupled using 3 molar excess of amino acid, 3 molar excess of HATU and 6 molar excess of DIEA, for duration of 2–16 hours, yielding two sub-libraries each contains 6 analogs.

The synthesis is illustrated in the following scheme:

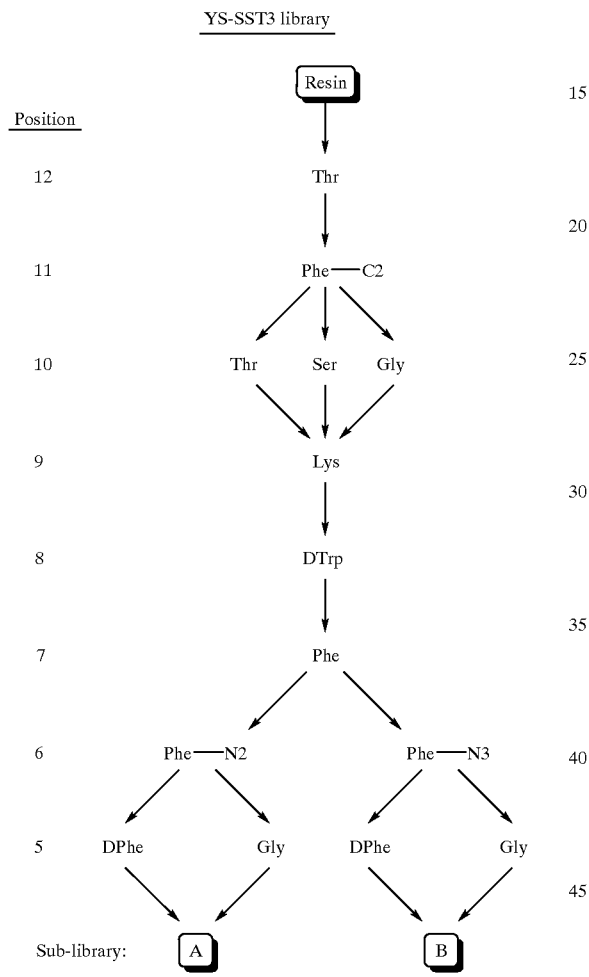

Example 20

YS-SST4 (A and B) LIBRARIES

In these libraries, the somatostatin peptides were synthesized in their reverse direction (from N- to C-terminal), and the amino acids in the sequence were reversed in their chirality (L-isomer instead of D and D-isomer instead of L) this was done based on the rational that one could reverse the sequence relative to the L-analog to retain the same biological surface. Two different libraries were produced: A—containing heptapeptides and B—containing octapeptides with additional Thr residue at the N-terminal. Each library consist of 24 different cyclic peptides.

The synthesis is illustrated in the following scheme:

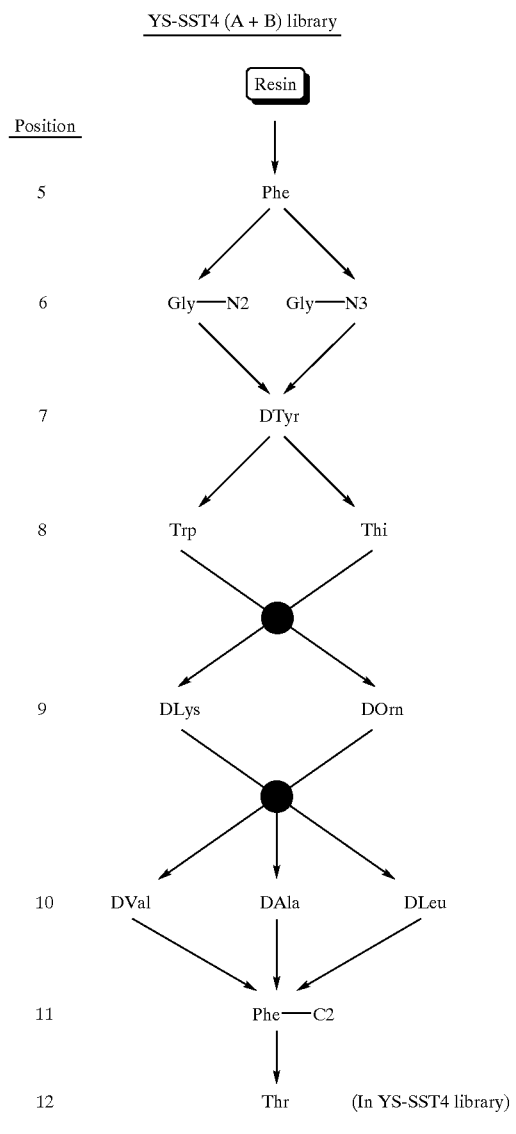

Example 21

YS-SST5 LIBRARY

This library was designed for optimization of bridge size and direction between positions 6 and 11 with simultaneous determination of the influence of various Naphtylalanine residues at position 5. The library consist of 4 sub-libraries with 16 peptides in each. The backbone-cyclic and the pre-cyclic libraries were synthesized simultaneously.

The following scheme describes the synthesis of the library.

YS-SST5 LIBRARY

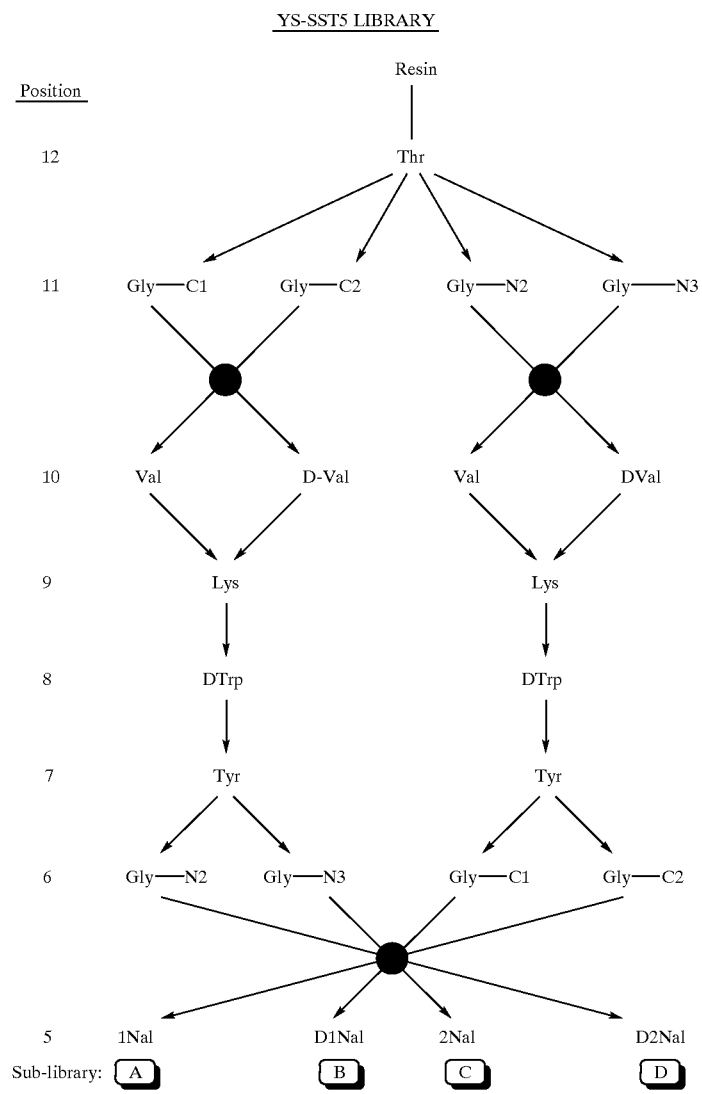

Example 22

VH-SST6 LIBRARY

This library of hexapeptides was synthesized with two different Phe-building units at position 6 and additional diversity at positions 7, 8 and 9. The peptides were cyclized between the back-bone of positions 6 and 10. Amino acids at positions 5 and 12 were omitted.

Example 23

VH-SST7 LIBRARY

This library contains 290304 backbone-cyclic peptides in 45 sub-libraries. The peptides were synthesized on non-cleavable resin (TentaGel-NH2), yielding bead-attached peptides for screening in solid-phase-assays. The composition of this library described in table VIII.

TABLE VIII

| | Composition of VH-SST7 library. | | | | | | | |
|---|---|---|---|---|---|---|---|---|
| Position | 5 | 6 | 7 | 8 | 9 | 10 | 11 | 12 |
| Groups | A | B | C | D | E | F | G | H |
| 1 | DPhe | Gly-N2 | Phe | Trp | Lys | Thr | Gly-C1 | Thr |
| 2 | Phg | Gly-N3 | Tyr | TiC | Arg | Val | Gly-C2 | Ser |
| 3 | 1Nal | Phe-N2 | Phg | | | Ser | Gly-C3 | Val |
| 4 | D1Nal | Ph2-N3 | pClPhe | | | Abu | Phe-C1 | 1Nal |
| 5 | 2Nal | Ala-N2 | pFPhe | | | | Phe-C2 | D1Nal |

TABLE VIII-continued

Composition of VH-SST7 library.

| Position | 5 | 6 | 7 | 8 | 9 | 10 | 11 | 12 |
|---|---|---|---|---|---|---|---|---|
| Groups | A | B | C | D | E | F | G | H |
| 6 | D2Nal | Ala-N3 | pNO$_2$Phe | | | | Phe-C3 | 2Nal |
| 7 | Thi | | | | | | | D2Nal |
| 8 | DThi | | | | | | | |
| 9 | pClPhe | | | | | | | |
| 10 | pFPhe | | | | | | | |
| 11 | pNO$_2$Phe | | | | | | | |
| 12 | Des | | | | | | | Total |
| Groups | 12 | 6 | 6 | 2 | 2 | 4 | 6 | 7 | 45 |
| Peptides per group | 24192 | 12096 | 12096 | 145152 | 145152 | 72576 | 12096 | 41472 | 290304 |

The sub-library are named for their defined position: $A^1$, $A^2$, ... $A^n$, $B^1$, ... $B^n$, ... $H^1$, $H^n$. For each group, positions other then the defined one, contain mixtures of amino acids. In each coupling step, each non-defined position gets a mixture of amino acids (total 1 molar equivalent of amino acids in each step in order to force the completion of each amino acid coupling and to eliminate kinetic effects, yielding non-equal presentation of peptides), that will be presented at this position. Identification of the most active sub-library in each of the A to H group, by solid-phase assay, will lead to the composition of most active backbone-cyclic peptide from the 290304 peptides presented in the library. The Rationale for Generation and Screening of New Somatostatin Libraries:

There are currently several known Somatostatin analogs in clinical use or in clinical trials. These include octapeptide analogs based on sequence 5–12 of the native peptide SRIF-14: Octreotide, RC-160, and Somatuline (Hofland et al., *Biochemical Pharmacology*, 50:287–297, 1995). These octapeptide analogs have been found to possess high affinity to SSTR2 and SSTR5. Another somatostatin analog, CGP 23996, which is based on sequence 3–13 of SRIF-14, binds selectively to SSTR1 and not to SSTR2. In addition, a diverse random octapeptide library has been disclosed (Wright et al., *Bio/Technology*, 13:165–169, 1995). This library revealed active peptides containing the Phe-Trp-Lys-Thr consensus sequence (positions 7–10 in SRIF-14) with additional Arg and Trp residues.

Libraries were synthesized according to the present invention, based on the expectation that the selectivity of binding of the somatostatin analogs to the different somatostatin receptor subtypes could be achieved by varying the SRIF-14 fragment that is chosen for backbone cyclization.

| | 1 | 2 | 3 | 4 | 5 | 6 | 7 | 8 | 9 | 10 | 11 | 12 | 13 | 14 |
|---|---|---|---|---|---|---|---|---|---|---|---|---|---|---|
| SRIF 14 | Ala | Gly | [Cys | Lys | Asn | Phe | Phe | Trp | Lys | Thr | Phe | Thr | Ser | Cys] |
| CGP 23996 | | c[ | Asu | Lys | Asn | Phe | Phe | Trp | Lys | Thr | Tyr | Thr | Ser] | |
| YS6A | Ala | Gly | [BU | Lys Arg | Asn DAsn | Phe | BU] | DTrp | Lys | NH$_2$ | | | | |
| YS6B | Ala D2Nal | [BU | Gly | Lys Arg | Asn DAsn | BU] | Phe | DTrp | Lys | NH$_2$ | | | | |
| Octreotide | | | | | | DPhe | Cys | Phe | DTrp | Lys | Thr | Cys | Thr | (O1) |
| "RC-160" | | | | | | DPhe | Cys | Tyr | DTrp | Lys | Val | Cys | Trp | NH$_2$ |
| Somatuline | | | | | | D2Nal | Cys | Tyr | DTrp | Lys | Val | Cys | Thr | NH$_2$ |
| Wright 1995 | | | | Cys | Arg | — | Phe | Phe | Trp | Lys | Thr | — | Trp | Cys |

Table III summarizes libraries that were cyclized via the backbone between positions 6 and 11 of the SRIF-14 sequence. These are constructed based on considerations of analogy to the known active octapeptide sequences listed above, and are designed to leave the consensus sequence intact, by accomplishing the cyclization outside the frame of residues 7 through 10.

Novel sequences were now also selected for cyclization via the backbone, and libraries were prepared from these sequences as described in the following Examples. These novel sequences are backbone cyclized between residues 2 and 6 or between residues 3 and 7 of the SRIF-14 sequence. This marks a departure from the assumption in the background art of the necessity of the consensus sequence Phe-Trp-Lys-Thr. Unexpectedly, these novel libraries have revealed biological activity, and receptor selectivity. These finding support the conclusion that the cyclization via the backbone can yield selective biologically active conformers, and the utility of the libraries in designing and preparing such conformers.

Example 24

YS-SST6 LIBRARY

This library comprises 128 backbone-cyclized somatostatin analogs in 8 sub-libraries and 128 precyclic analogs in 8 additional sub-libraries. Two basic cyclizations were used: position 3 to position 7 and position 2 to position 6. Each sub-library differs in the bridge location, bridge type, and direction or amino acid at position 1 (Ala or D2Nal).

The backbone cyclized and precyclic sub-libraries were tested for their inhibition of $^{125}$I-SRIF binding to mouse pituitary AtT20 cells. The results of these experiments are summarized in Table IX. Unexpectedly, there was considerable activity of these novel analogs that do not contain the consensus sequence, in terms of specific inhibition of SRIF binding.

spanning different parts of the SRIF structure. Each octapeptide sub-library is shifted from the next by one residue. Thus, the first sub-library spans residues 7 to 14 of SRIF-14, the second sub-library spans residues 6 to 13 of SRIF-14, and so on. Thus, this library comprises a total of 14 overlapping backbone-cyclized octapeptides with a shift of one residue between sub-library. The synthesis is achieved by simultaneous synthesis of the analogs from different starting points, such that the coupling of the building units is performed for all of the sub-libraries at the same time. In all of these sub-libraries, the backbone cyclization is accomplished

TABLE IX

Structure and activity of YS-SST6 libraries.

| Sub-lib. | 1 | 2 | 3 | 4 | 5 | 6 | 7 | 8 | 9 | | AtT20 % inhibition of $^{125}$I-SRIF binding | | |
|---|---|---|---|---|---|---|---|---|---|---|---|---|---|
| | | | | | | | | | | | $10^{-8}$M | $10^{-7}$M | $10^{-6}$M |
| A1 | Ala | Gly | Gly-C1 | Lys | Asn | Phe | Gly-N2 | DTrp | Lys | C | 42 | 91 | 103 |
| | | | Gly-C2 | Arg | DAsn | | Gly-N3 | | | P | 54 | 73 | 105 |
| A2 | D2Nal | Gly | Gly-C1 | Lys | Asn | Phe | Gly-N2 | DTrp | Lys | C | 72 | 57 | 72 |
| | | | Gly-C2 | Arg | DAsn | | Gly-N3 | | | P | 46 | 88 | 97 |
| A3 | Ala | Gly | Gly-N2 | Lys | Asn | Phe | Gly-C1 | DTrp | Lys | C | 44 | 60 | 76 |
| | | | Gly-N3 | Arg | DAsn | | Gly-C2 | | | P | 27 | 34 | 86 |
| A4 | D2Nal | Gly | Gly-N2 | Lys | Asn | Phe | Gly-C1 | DTrp | Lys | C | 51 | 69 | 96 |
| | | | Gly-N3 | Arg | DAsn | | Gly-C2 | | | P | | 31 | 80 |
| B1 | Ala | Gly-C1 | Gly | Lys | Asn | Gly-N2 | Phe | DTrp | Lys | C | 10 | 54 | 77 |
| | | Gly-C2 | | Arg | DAsn | Gly-N3 | | | | P | 50 | 36 | 88 |
| B2 | D2Nal | Gly-C1 | Gly | Lys | Asn | Gly-N2 | Phe | DTrp | Lys | C | 13 | 52 | 86 |
| | | Gly-C2 | | Arg | DAsn | Gly-N3 | | | | P | 16 | 37 | 74 |
| B3 | Ala | Gly-N2 | Gly | Lys | Asn | Gly-C1 | Phe | DTrp | Lys | C | 31 | 66 | 52 |
| | | Gly-N3 | | Arg | DAsn | Gly-C2 | | | | P | 12 | 37 | 86 |
| B4 | D2Nal | Gly-N2 | Gly | Lys | Asn | Gly-C1 | Phe | DTrp | Lys | C | 6 | 81 | 101 |
| | | Gly-N3 | | Arg | DAsn | Gly-C2 | | | | P | 45 | 83 | 98 |

Example 25
IG-SST9 LIBRARY

In order to more systematically test the necessity of any given frame in the SRIF sequence for biological activity of the analogs, it was decided to synthesize in parallel a library of octapeptide analogs that differ from one another in between one glycine C2 unit distal to the N terminal of the peptide sequence and one glycine N3 unit proximal to the N terminal end of the peptide sequence.

Library IG-SST9 is represented in the following scheme:

IG-SST9 Library

```
                        RESIN
                          │
                          ▼
              14   Phe   RESIN
                    │      │
                    ▼      ▼
              13   Ser    Ser    RESIN
                    │      │       │
                    ▼      ▼       ▼
              12   GC2    GC2    Thr    RESIN
                    │      │       │       │
                    ▼      ▼       ▼       ▼
              11   Phe    Phe    Phe    Phe    RESIN
                    │      │       │       │      │
                    ▼      ▼       ▼       ▼      ▼
```

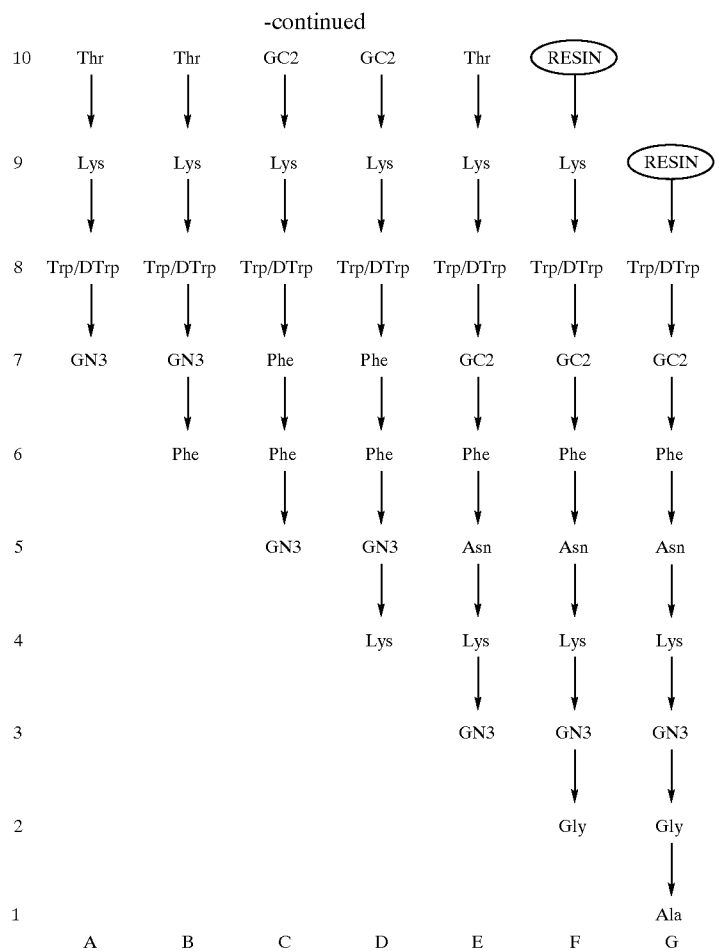

Example 26
SST11 LIBRARY

Different phenylalanine building units (PheBU: Phe-N2, Phe-N3, Phe-C2, Phe-C3) are used in this library as bridging arms for the generation of backbone-cyclized analogs of SRIF-14 sequence 4–11 (sub-library D in library IG-SST9). In addition, the non-bridging Phe residue (position 6 or 7) is substituted with various Phe and Nal derivatives: DPhe, pNO$_2$Phe, pClPhe, pFPhe, phenylglycine (Phg), DPhg, L2Nal, D2Nal. This provides a library of 18 groups with 16 analogs per group as described in the following representation:

| 4 | 5 | 6 | 7 | 8 | 9 | 10 | 11 |
|---|---|---|---|---|---|---|---|
| Lys | Asn | Phe | Phe | Trp | Lys | Thr | PheBU (4) |
| DLys | | PheBU (4) | PheBU (4) | DTrp | | | |
| | | DPhe | DPhe | | | | |
| | | pNO$_2$Phe | pNO$_2$Phe | | | | |
| | | pClPhe | pClPhe | | | | |
| | | pFPhe | pFPhe | | | | |
| | | Phg | Phg | | | | |
| | | DPhg | DPhg | | | | |
| | | L2Nal | L2Nal | | | | |
| | | D2Na | D2Na | | | | |

INTERLEUKIN-6 RECEPTOR PEPTIDE LIBRARIES:

Interleukin-6 (IL-6), also known as interferon-beta-2, is a pleiotropic cytokine, which acts as a growth and differentiation factor for a number of cell types. Overproduction of IL-6 has been implicated in the pathogenesis of multiple myeloma and in post-menopausal osteoporosis. Inhibition of the action of IL-6 should be of clinical benefit in the treatment of multiple myelomas, a malignancy in which the growth stimulatory effect of IL-6 contributes to tumor growth.

IL-6 is believed to interact sequentially with two transmembrane receptors, the low affinity IL-6 receptor (IL-6R alpha, also denoted gp80) and the signal transducer gp130, via distinct binding sites. The gp130 protein is also involved in signal transduction of a number of other growth factors or hormones (reviewed by Hirano et al., Stem Cells 12, 262–277, 1994).

It has been disclosed by Savino et al. (EMBO J. 13, 5863–5870, 1994; EMBO J. 13, 1357–1367, 1994), that site directed mutagenesis of IL-6 residues that are presumed to interact with the gp130 subunit, can yield antagonists that maintain unimpaired affinity to IL-6R alpha but no bioactivity due to inability to bind to gp130. Mutation of residues A229 and N231 were shown to prevent IL-6 signaling.

It has been further disclosed that inhibitory peptides may be designed to prevent interaction of IL-6 and its receptor. Grube and Cochrane (J. Biol. Chem. 269, 20791–20797, 1994) disclose a deca-peptide spanning residues 249 through 258 of the IL-6R molecule which is active in preventing the bioactivity of IL-6. This peptide, is more active then the 16-amino acids sequence Y249-T264. According to this disclosure, the four arginine residues corresponding to positions 250, 252, 256 and 258 of the receptor sequence are essential for IL-6 inhibition. In the following depiction of the sequences involved in the inhibition of IL-6, the underlined residues are those considered as essential:

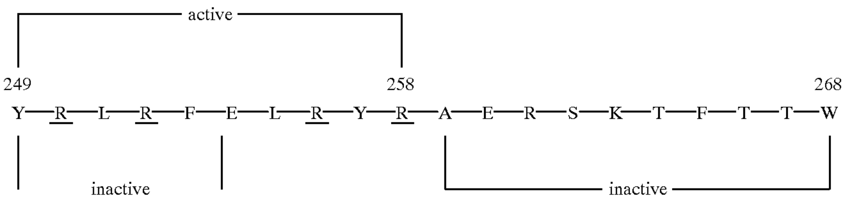

Additional studies have shown that a peptide starting with leucine 255 of the IL-6R and extending beyond the known inhibitory peptide (249 through 258 of the IL-6R) towards the carboxy terminus, i.e., at the 3' side, is also an effective inhibitor (Revel et al., 1995), indicating that not all four arginines are necessary for the inhibitory activity of this peptide sequence.

According to the present invention, libraries are designed to provide backbone cyclized peptidomimetics based on these and other novel peptide sequences to optimally inhibit IL-6 bioactivity without disrupting normal cell functions, including those mediated via gp130 activation by other growth factors or immunomodulators. Backbone cyclized peptidomimetics are disclosed that achieve improved metabolic stability and oral bioavailability without interfering with the residues identified as essential for inhibitory function, of these peptides.

Suitable targets for inhibition by peptidomimetics according to the present invention will include : 1) the interface between the IL-6 molecule and IL-6R; 2) the interface between IL-6 and gp130; 3) the interface between IL-6R and gp130. The peptide sequences to be modified are derived either from the IL-6R molecule, or from the IL-6 molecule itself.

Libraries of backbone cyclized peptidomimetics will be screened for inhibitory activity in known test systems for IL-6 action. The most active compounds will be isolated from the pooled libraries following individual assay. The IL-6 response can be conveniently measured in terms of growth inhibition of myeloleukemic Ml cells. A well calibrated dose dependent inhibition of growth measured after 3 days of culture provides a quantitative assay of IL-6 action. Other cell types such as myelomas are growth stimulated and can also be used to quantitate the response to IL-6.

In order to optimize the activity, the length and cyclization state of the peptides is varied in order to mimic the conformation of the peptides as predicted by three dimensional computer models.

The initial libraries, are designed with the aim of identifying the best cyclization location and size within linear peptides derived from sequences 249–264 particularly 249–258 and 255–264 and peptides derived from other candidate contact positions of the IL-6R, the IL-6 and the gp130 molecules.

Example 27

The first backbone-cyclic peptide library of residues 255–264 (YK-IL(1), contains 11 sub-libraries differ in the cyclization points as described in table X, leaving the Arg256, 258,261 unchanged and substituting the cyclization points amino acids with Gly-building units. The shortest distance between two bridgeheads is 5 amino acids.

TABLE X

Different cyclization points of YK-ILϕ1 library

| | | | |
|---|---|---|---|
| 255–259 | 257–262 | 259–263 | 260–264 |
| 255–260 | 257–263 | 259–264 | |
| 255–262 | 257–264 | | |
| 255–263 | | | |
| 255–264 | | | |

Each sub-library contain 12 peptide with different building units at the cyclization points as indicated in Table XI.

TABLE XI

Peptides containing different bridge type and size

| | C-terminal unit | | | | |
|---|---|---|---|---|---|
| N-terminal unit | Gly-C1 | Gly-C2 | Gly-C3 | Gly-N2 | Gly-N3 |
| Gly-N2 | N2-C1 | N2-C2 | N2-C3 | | |
| Gly-N3 | N3-C1 | N3-C2 | N3-C3 | | |
| Gly-C1 | | | | C1-N2 | C1-N3 |
| Gly-C2 | | | | C2-N2 | C2-N3 |
| Gly-C3 | | | | C3-N2 | C3-N3 |

Example 28

The second library is synthesized with the use of Arg-building units as cyclization points at positions 256, 258, 261 and use of the original sequence (Leu255, Ala259, etc.) modified amino acids as building units additional libraries are synthesized based on the biological information obtain from screening the initial libraries, using additional types of building units and substitution of other sequence amino acids.

Example 29

The initial backbone-cyclic library of the 249–258 peptide (YK-IL(2), is composed of 7 sub-libraries, differ in the cyclization points (249–257, 249–255, 249–254, 257–253, 251–257, 251–255, 253–257), leaving the Arg250, 252,256, 258 unchanged and substituting the cyclization points amino acids with 6 different Gly-building units yielding 12 peptides differ in their bridge, in each sub-library. The shortest distance between two bridgeheads is 5 amino acids.

In addition, backbone cyclic peptide libraries composed of shorter peptides of the above sequences (249–258 and 255–264), are synthesized with systematic deletions of amino acids that are not essential for activity.

What is claimed is:

1. A library of chemical compounds comprising a mixture of conformationally constrained backbone-cyclized peptide analogs, each analog comprising a peptide sequence having at least one building unit comprising an N^α-derivative of an amino acid, wherein at least one backbone nitrogen of a first amino acid in each said peptide sequence is linked by a bridging group to a terminus located at either a side chain of at least one other amino acid in said peptide sequence or to at least one other backbone nitrogen in said peptide sequence, with the bridging group comprising a disulfide, amide, thioether, thioester, imine, ether, or alkene, to form a backbone-cyclized peptide analog, wherein at least some of the analogs have the same peptide sequence but differ from the others in that (a) the bridging group is positioned on a different backbone nitrogen, or (b) the bridging group is different; and wherein the bridging group spans at least two amino acids of the peptide sequence in addition to its linkage to the backbone nitrogen of the first amino acid and the bridging group's terminus.

2. The library of claim 1 wherein at least one of said building units is located other than at the end of the peptide sequence.

3. The library of claim 1 wherein none of said building units is located at the end of the peptide sequence.

4. The library of claim 1 comprising a plurality of backbone-cyclized peptide analogs, wherein at least two backbone nitrogens in each peptide sequence are linked together to form a peptide analog having the general formula (I):

Formula (I)

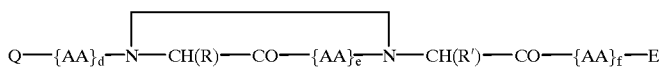

wherein:
  d, e, and f each independently designates 0 or an integer from 1 to 10; each {AA} designates an amino acid residue or the residue of a plurality of amino acids linked together through peptide bonding, wherein each {AA} may be the same or different; Q represents H or an acyl group; E represents a hydroxyl group, a carboxyl protecting group or an amino group, or the carboxy terminal group CO-E, wherein the CO is part of {AA}, can be reduced to CH$_2$—OH or CHO; each of R and R' is independently hydrogen or an amino acid side-chain optionally bound with a specific protecting group; and the lines designate a bridging group of the formula:
  (i) -X-M-Y-W-Z-; or
  (ii) -X-M-Z—
    wherein: M and W are independently selected from the group consisting of disulfide, amide, thioether, thioester, imine, ether, and alkene; and X, Y and Z are each independently selected from the group consisting of alkylene, substituted alkylene, arylene, homo- or hetero-cycloalkylene and, substituted cycloalkylene.

5. The library of claim 4 wherein -X-M-Y-W-Z- is: —(CH2)x-M-(CH2)y-W-(CH2)z- wherein M and W are as recited above; x and z each independently designates an integer of from 1 to 10, and y is zero or an integer of from 1 to 8, with the proviso that if y is zero, W is absent.

6. The library of claim 1 comprising a plurality of backbone-cyclized peptide analogs, wherein the backbone of each analog is cyclized to a side-chain of an amino acid to form a peptide analog of the general formula (II):

Formula (II)

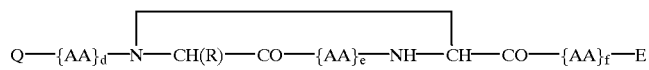

wherein:
  d, e, and f each independently designates 0 or an integer from 1 to 10; each {AA} designates an amino acid residue or the residue of a plurality of amino acids linked together through peptide bonding, wherein each {AA} may be the same or different; Q represents H or an acyl group; E represents a hydroxyl group, a carboxyl protecting or an amino group, or CO-E, wherein the CO is part of {AA}, can be reduced to CH$_2$—OH; R is an amino acid side chain optionally bound with a specific protecting group; and the line designates a bridging group of the formula:
  (i) -X-M-Y-W-Z-; or
  (ii) -X-M-Z—
    wherein M and W are independently selected from the group consisting of disulfide, amide, thioether, imine, ether, and alkene; X, Y and Z are each independently selected from the group consisting of alkylene, substituted alkylene, arylene, cycloalkylene and substituted cycloalkylene.

7. The library of claim 6 wherein -X-M-Y-W-Z- is: —(CH2)x-M-(CH2)y-W-(CH2)z- wherein M and W are as recited above; x and z each independently designates an integer of from 1 to 10, and y is zero or an integer of from 1 to 8, with the proviso that if y is zero, W is absent.

8. The library of claim 1 comprising a mixture of backbone-cyclized bicyclic peptide analogs, each of which comprises a plurality of building units comprising an N^α-derivative of an amino acid.

9. The library of claim 8 comprising a mixture of backbone-cyclized peptide analogs each having the general formula (III):

Formula (III)

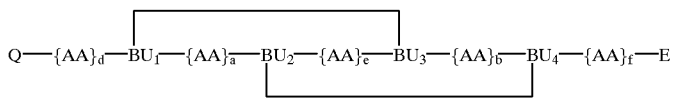

wherein: a and b each independently designates an integer from 1 to 8 or zero; d, e, and f each independently designates an integer from 1 to 10 or zero; each {AA} designates an amino acid residue —HN—CH(R)—CO— wherein R is an amino acid side chain, optionally bound with a specific protecting group, and the amino acid residues in each chain may be the same or different; Q represents H or an acyl group; E represents a hydroxyl group, a carboxyl protecting group or an amino group, or the carboxy terminal group CO-E, wherein the CO is part of {AA}, can be reduced to $CH_2$—OH or CHO; BU represents an $N^\alpha$-ω-functionalized derivative of amino acids of formula (IV):

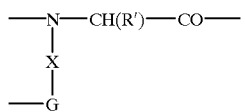

Formula (IV)

wherein:
X is a spacer group selected from the group consisting of alkylene, substituted alkylene, arylene, cycloalkylene and substituted cycloalkylene; R' is an amino acid side chain, optionally bound with a specific protecting group; and G is a functional group selected from the group consisting of amines, thiols, alcohols, carboxylic acids and esters, and alkyl halides; which is incorporated into the peptide sequence and subsequently selectively cyclized via the functional group G with one of the side chains of the amino acids in said peptide sequence or with another ω-functionalized amino acid derivative; and the lines in formula II designate (a) two separate hydrogen substituents or (b) a bridging group of the formula:
(i) -X-M-Y-W-Z-; or
(ii) -X-M-Z—
provided that at least one of the lines is a bridging group of (i) or (ii), wherein: M and W are independently selected from the group consisting of disulfide, amide, thioether, thioester, imine, ether, and alkene; and X, Y and Z are each independently selected from the group consisting of alkylene, substituted alkylene, arylene, homo-cycloalkylene, or hetero-cycloalkylene and substituted cycloalkylene.

10. The library according to one of claims 4, 6, or 8 that has at least four members and wherein at least some of the analogs are bradykinin analogs, Substance P analogs, BPI analogs, somatostatin analogs, or interleukin-6 inhibitory peptide analogs.

11. The library according to one of claims 1, 4, 6, or 8 comprising two or more sublibraries, each containing a plurality of peptide analogs.

12. The library of claim 1 wherein all the analogs have the same peptide sequence but differ in their bridging groups.

13. The library of claim 9 wherein all the analogs have the same peptide sequence but differ in their bridging groups.

14. A method for the preparation of a library of chemical compounds comprising a mixture of conformationally constrained backbone-cyclized peptide analogs, each analog comprising a peptide sequence having at least one building unit comprising an $N^\alpha$-derivative of an amino acid, wherein at least one backbone nitrogen of a first amino acid in each said peptide sequence is linked by a bridging group to a terminus located at either a side chain of at least one other amino acid in said peptide sequence or to at least one other backbone nitrogen in said peptide sequence, with the bridging group comprising a disulfide, amide, thioether, thioester, imine, ether, or alkene, to form a backbone-cyclized peptide analog, wherein at least some of the analogs have the same peptide sequence but differ from the others in that (a) the bridging group is positioned on a different backbone nitrogen or (b) the bridging group is different; and wherein the bridging group spans at least two amino acids of the peptide sequence in addition to its linkage to the backbone nitrogen of the first amino acid and the bridging groups terminus, said method comprising the steps of:

providing peptide sequences having a plurality of building units containing amino acids and linked nitrogen atoms;

incorporating into each peptide sequence at least one $N^\alpha$-ω-functionalized derivative of an amino acid of formula (IV):

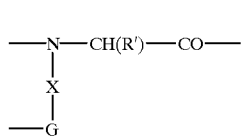

Formula (IV)

wherein: X is a spacer group selected from the group consisting of alkylene, substituted alkylene, arylene, cycloalkylene and substituted cycloalkylene; R' is an amino acid side chain, optionally bound with a specific protecting group; and G is a functional group selected from the group consisting of amines, thiols, alcohols, carboxylic acids and esters, aldehydes, alcohols and alkyl halides, by selectively cyclizing a functional group G with another ω-functionalized amino acid derivative or with one of the side chains of the amino acids in said peptide sequence to form conformationally constrained backbone-cyclized peptide analogs; and mixing a plurality of said analogs together to generate the library.

15. A method as in claim 14 for the preparation of a library of a plurality of backbone-cyclized peptide analogs of the general Formula (I):

Formula (I)

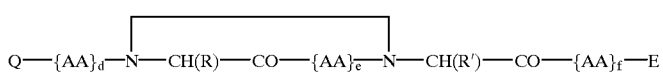

wherein: d, e, and f each independently designates an integer from 1 to 10; each (AA) designates an amino acid residue wherein the amino acid residues in each chain may be the same or different; Q represents H or an acyl group; E represents a hydroxyl group, a carboxyl protecting group or an amino group, or the carboxy terminal group CO-E, wherein the CO is part of {AA}, can be reduced to $CH_2$—OH; R and R' each designates an amino acid side-chain optionally bound with a specific protecting group; and the line designates a bridging group of the formula:

(i) -X-M-Y-W-Z-; or (ii) -X-M-Z— wherein: M and W are independently selected from the group consisting of disulfide, amide, thioether, thioester, imine, ether, and alkene; and X, Y and Z are each independently selected from the group consisting of alkylene, substituted alkylene, arylene, homo- or hetero-cycloalkylene and substituted cycloalkylene; comprising the steps of:

providing peptide sequences having a plurality of building units containing amino acids and linked nitrogen atoms;

incorporating into each peptide sequence the at least one $N^\alpha$-ω-functionalized derivative of an amino acid of formula (IV);

Formula (IV)

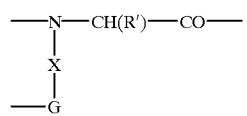

by selectively cyclizing the functional group G with another ω-functionalized amino acid derivative to form the backbone-cyclized peptide analogs.

16. The method of claim 15 wherein G is an amine, thiol, or carboxyl group.

17. A method as in claim 14 for the preparation of a library of a plurality of backbone-cyclized peptide analogs of the general formula (II):

Formula (II)

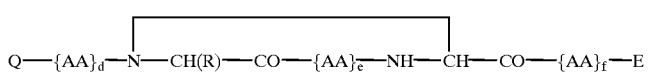

wherein d, e and f each independently designates an integer from 1 to 10; each {AA} designates an amino acid residue wherein the amino acid residues in each chain may be the same or different; Q represents H or an acyl group; E represents a hydroxyl group, a carboxyl protecting or an amino group, or CO-E, wherein the CO is part of {AA}, can be reduced to $CH_2$—OH; R is an amino acid side chain optionally bound with a specific protecting group; and the line designates a bridging group of the Formula:

(i) -X-M-Y-W-Z-; or (ii) -X-M-Z— wherein M and W are independently selected from the group consisting of disulfide, amide, thioether, thioester, imine, ether, and alkene; X, Y and Z are each independently selected from the group consisting of alkylene, substituted alkylene, arylene, homo- or hetero-cycloalkylene and substituted cycloalkylene; comprising the steps of:

providing peptide sequences having a plurality of building units containing amino acids and linked nitrogen atoms;

incorporating into each peptide sequence the at least one ω-functionalized derivative of an amino acid of formula (IV);

Formula (IV)

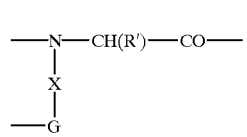

by selectively cyclizing the functional group G with one of the side chains of the amino acids in said peptide sequence to form the backbone-cyclized peptide analogs.

18. The method of claim 17 wherein G is a carboxyl group or a thiol group.

19. The method of one of claims 15 or 17, wherein R is CH3—, (CH3)2CH—, (CH3)2CHCH2—, CH3CH2CH(CH3)—, CH3S(CH2)2—, HOCH2—, CH3CH(OH)—, HSCH2—, NH2C(=O)CH2—, NH2C(=O)(CH2)2—, NH2(CH2)3—, HOC(=O)CH2—, HOC(=O)(CH2)2—, NH2(CH2)4—, C(NH2)2NH(CH2)3—, HO-phenyl-CH2—, benzyl, methylindole, or methylimidazole.

20. A method as in claim 14, wherein the library comprises a mixture of backbone-cyclized bicyclic peptide analogs, each of which comprises a plurality of building units comprising an $N^\alpha$-derivative of an amino acid.

21. The method of any one of claims 15, 17, or 20 wherein said peptide sequences are provided covalently coupled to an insoluble polymeric support.

22. A method as in claim 20 for the preparation of a library of a plurality of conformationally constrained backbone-cyclized peptide analogs of the general Formula (III):

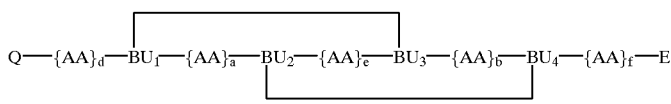

Formula (III)

wherein: a and b each independently designates an integer from 1 to 8 or zero; d, e, and f each independently designates an integer from 1 to 10; each {AA} designates an amino acid residue wherein the amino acid residues in each chain may be the same or different; Q represents H or an acyl group; E represents a hydroxyl group, a carboxyl protecting group or an amino group, or the carboxy terminal group CO-E, wherein CO is part of {AA}, can be reduced to $CH_2$—OH; R and R' each designates an amino acid side-chain optionally bound with a specific protecting group; BU represents an $N^\alpha$-$\omega$-functionalized derivative of amino acids of formula (IV):

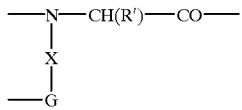

Formula (IV)

wherein X is a spacer group selected from the group consisting of alkylene, substituted alkylene, arylene, cycloalkylene and substituted cycloalkylene; R' is an amino acid side chain, optionally bound with a specific protecting group; and G is a functional group selected from the group consisting of amines, thiols, alcohols, carboxylic acids and esters, and alkyl halides; and the lines in formula III designate (a) two separate hydrogen substituents or (b) a bridging group of the formula:

(i) -X-M-Y-W-Z-; or
(ii) X-M-Z—
provided that at least one of the lines is a bridging group of (i) or (ii), wherein:

M and W are independently selected from the group consisting of disulfide, amide, thioether, thioester, imine, ether, and alkene; and X, Y and Z are each independently selected from the group consisting of alkylene, substituted alkylene, arylene, homo- or heterocycloalkylene and substituted cycloalkylene; comprising the steps of:

providing peptide sequences having a plurality of building units containing amino acids and linked nitrogen atoms;

incorporating into each peptide sequence the at least one $N^\alpha$-$\omega$-functionalized derivative of an amino acid of Formula (IV) by selectively cyclizing a functional group G with another $\omega$-functionalized amino acid derivative or with one of the side chains of the amino acids in said peptide sequence to form backbone-cyclized peptide analogs; and further cyclizing a second functional group G with yet another $\omega$-functionalized amino acid derivative or with one of the side chains of the amino acids in said peptide sequence to form the conformationally constrained backbone-cyclized bicyclic peptide analogs.

23. The method of claim 22 which further comprises associating different analogs in the library which all have the same peptide sequence but differ in their bridging groups.

24. The method of claim 14 which farther comprises associating different analogs in the library which all have the same peptide sequence but differ in their bridging groups.

* * * * *

UNITED STATES PATENT AND TRADEMARK OFFICE
CERTIFICATE OF CORRECTION

PATENT NO. : 6,117,974

DATED : September 12, 2000

INVENTOR(S) : Gilon et al.

It is certified that error appears in the above-identified patent and that said Letters Patent is hereby corrected as shown below:

Column 57, line 40 (claim 9, line 43): change "formula II" to --formula III--.

Column 58, line 29 (claim 14, line 29): change "groups" to --group's--.

Column 62, line 33 (claim 23, line 1): change "22" to --21--.

Signed and Sealed this

Twenty-fourth Day of April, 2001

Attest:

NICHOLAS P. GODICI

Attesting Officer

Acting Director of the United States Patent and Trademark Office

UNITED STATES PATENT AND TRADEMARK OFFICE
CERTIFICATE OF CORRECTION

Page 1 of 2

PATENT NO. : 6,117,974

DATED : September 12, 2000

INVENTOR(S) : Gilon et al.

It is certified that error appears in the above-identified patent and that said Letters Patent is hereby corrected as shown below:

In the abstract, cover page, lines 5 and 8, change "N(((-" to -- $N^{\alpha}$-ω- --.

Column 5, lines 53-58, change the chemical formulae as follows: --$CH_3$—, $(CH_3)_2CH$—, $(CH_3)_2CHCH_2$—, $CH_3CH_2CH(CH_3)$—, $CH_3S(CH_2)_2$—, $HOCH_2$—, $CH_3CH(OH)$—, $HSCH_2$—, $NH_2C(=O)CH_2$—, $NH_2C(=O)(CH_2)_2$—, $NH2(CH_2)_3$—, $HOC(=O)CH_2$—, $HOC(=O)(CH_2)_2$—, $NH_2(CH_2)_4$—, $C(NH_2)_2NH(CH_2)_3$—, HO-phenyl-$CH_2$—,--.

Column 12, line 46: change "w-thiol" to --ω-thiol--.

Column 12, line 65: change "a-amine to --α-amine--.

Column 35, line 35: change "125I" to --$125^I$--.

Column 36, line 32: change "125I" to --$125^I$--.

Column 39, line 23: change "125I" to --$125^I$--. .

Column 41, line 52: change "125I" to --$125^I$--. .

Column 53, lines 13 and 14: change "|     active     |" to --|_____active_____|--.

Column 55," —(CH2)x-M-(CH2)y-W-(CH2)z-" to -- —$(Ch_2)_x$-M-$(CH_2)_y$-W-$(CH_2)_z$- --.

Column 56," —(Ch2)x-M-(CH2)y-W-(CH2)z-" to -- —$(Ch_2)_x$-M-$(CH_2)_y$-W-$(CH_2)_z$- --.

UNITED STATES PATENT AND TRADEMARK OFFICE
CERTIFICATE OF CORRECTION

PATENT NO. : 6,117,974          Page 2 of 2

DATED : September 12, 2000

INVENTOR(S) : Gilon et al.

It is certified that error appears in the above-identified patent and that said Letters Patent is hereby corrected as shown below:

Column 60, lines 39-44, change the chemical formulae as follows: --$CH_3$--, $(CH_3)_2CH$--, $(CH_3)_2CHCH_2$--, $CH_3CH_2CH(CH_3)$--, $CH_3S(CH_2)_2$--, $HOCH_2$--, $CH_3CH(OH)$--, $HSCH_2$--, $NH_2C(=O)CH_2$--, $NH_2C(=O)(CH_2)_2$--, $NH_2(CH_2)_3$--, $HOC(=O)CH_2$--, $HOC(=O)(CH_2)_2$--, $NH_2(CH_2)_4$--, $C(NH_2)_2NH(CH_2)_3$--, HO-phenyl-$CH_2$--,--.

Signed and Sealed this

Eighth Day of May, 2001

NICHOLAS P. GODICI

Attest:

Attesting Officer      Acting Director of the United States Patent and Trademark Office